(12) United States Patent
Kennedy et al.

(10) Patent No.: US 9,708,455 B2
(45) Date of Patent: Jul. 18, 2017

(54) POROUS ELECTROLYTIC POLYMER CRYOGELS FOR ENHANCED ELECTRICAL COLLAPSIBILITY

(71) Applicant: PRESIDENT AND FELLOWS OF HARVARD COLLEGE, Cambridge, MA (US)

(72) Inventors: Stephen Michael Kennedy, Somerville, MA (US); Sidi Ahmed Bencherif, Boston, MA (US); David J. Mooney, Sudbury, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

(21) Appl. No.: 14/418,599

(22) PCT Filed: Aug. 2, 2013

(86) PCT No.: PCT/US2013/053367
§ 371 (c)(1),
(2) Date: Jan. 30, 2015

(87) PCT Pub. No.: WO2014/022749
PCT Pub. Date: Feb. 6, 2014

(65) Prior Publication Data
US 2015/0299415 A1   Oct. 22, 2015

Related U.S. Application Data

(60) Provisional application No. 61/678,734, filed on Aug. 2, 2012.

(51) Int. Cl.
*A61K 9/00* (2006.01)
*C08J 9/28* (2006.01)
*A61K 9/06* (2006.01)
*C08F 220/06* (2006.01)
*C08F 220/56* (2006.01)
*C08F 222/10* (2006.01)

(52) U.S. Cl.
CPC .............. *C08J 9/286* (2013.01); *A61K 9/0009* (2013.01); *A61K 9/06* (2013.01); *C08F 220/06* (2013.01); *C08F 220/56* (2013.01); *C08J 9/28* (2013.01); *C08F 2222/1013* (2013.01); *C08J 2201/0484* (2013.01); *C08J 2205/022* (2013.01); *C08J 2207/10* (2013.01); *C08J 2333/02* (2013.01); *C08J 2333/26* (2013.01); *C08J 2343/00* (2013.01); *C08J 2347/00* (2013.01)

(58) Field of Classification Search
USPC .......................................................... 424/400
See application file for complete search history.

(56) References Cited

U.S. PATENT DOCUMENTS

| 2005/0019770 | A1 | 1/2005 | Mattiasson et al. |
| 2009/0170973 | A1 | 7/2009 | Mattiasson et al. |
| 2011/0028599 | A1 | 2/2011 | Costantino et al. |
| 2011/0230567 | A1 | 9/2011 | Stromme et al. |
| 2011/0262489 | A1 | 10/2011 | Zhao |

OTHER PUBLICATIONS

Shukla (Ind. Eng. Chem. Res. 2011, 50, 10918-10927; publication date, Aug. 22, 2011).*

* cited by examiner

*Primary Examiner* — Devang Thakor
(74) *Attorney, Agent, or Firm* — McCarter & English, LLP; Maria Laccotripe Zacharakis; Deborah L. Nagle

(57) ABSTRACT

The invention provides cryogels whose porosity, pore size, pore connectivity, swelling agent concentration, and/or specific volume undergoes a change from a first value to a second value in response to an electrical stimulus. The cryogels have interconnected macropores which greatly enhance their ability to rapidly undergo volumetric collapse when subjected to moderate electric fields. The cryogels of the invention can be easily integrated into arrays capable of rapid configurational and chromatic optical modulations, and when loaded with drugs, are able to coordinate the delivery profile of multiple drugs. The cryogel can be prepared by polymerizing an aqueous solution of charged monomers and cross-linker monomers at a temperature below the freezing temperature of the solvent.

25 Claims, 20 Drawing Sheets

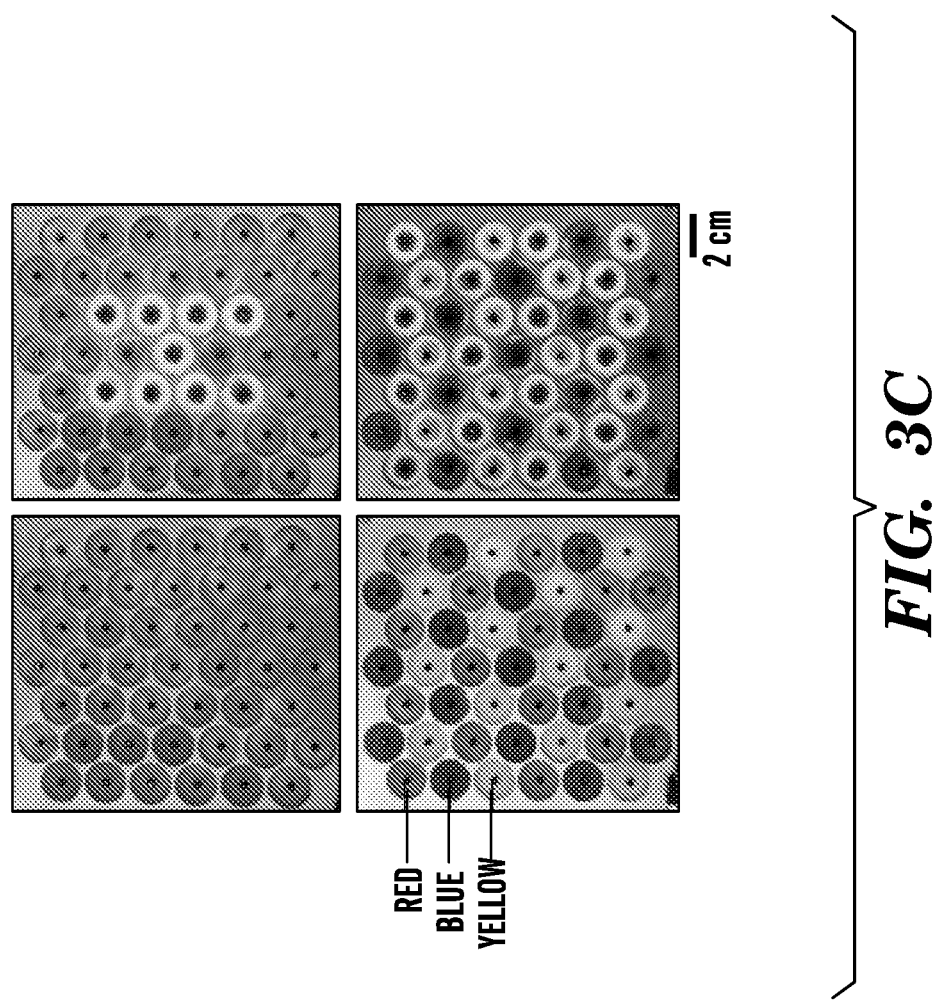

POROUS ELECTROLYTIC POLYMER CRYOGELS FOR ENHANCED ELECTRICAL COLLAPSIBILITY

CROSS REFERENCE TO RELATED APPLICATIONS

This application is a 35 U.S.C. §371 National Phase Entry Application of International Application No. PCT/US2013/053367 filed Aug. 2, 2013, which designates the US, and which claims benefit under 35 U.S.C. §119(e) of U.S. Provisional Application No. 61/678,734 filed Aug. 2, 2012, the contents of which is incorporated herein by reference in their entirety.

GOVERNMENT SUPPORT

This invention was made with government support under grant no. W911NF-10-1-0113 awarded by Defense Advanced Research Projects Agency (U.S. Army/MRMC), grant no. 2 R01 DE013349 awarded by the National Institutes of Health, and grant no. DMR-1005022 awarded by the National Science Foundation. The government has certain rights in the invention.

TECHNICAL FIELD

The present disclosure relates generally to materials that can rapidly vary their porosity, pore size, pore connectivity, swelling agent concentration, and/or specific volume in response to an electrical stimulus. This disclosure further relates to use of these materials for control release drug and delivery.

BACKGROUND

Stimulus-responsive hydrogels hold potential utility in numerous areas including, but not limited to, robotic actuation, microfluidic control, sensory technology, optical devices, drug delivery, and tissue engineering. Electrically responsive hydrogels, in particular, are desirable due to their potential compatibility with electrical circuitry and subsequent amenability to microprocessor-based control. This, in turn, affords these materials the ability to be controlled in scenarios requiring complex and precise timing—such as those aforementioned. Despite such promise, electrically responsive hydrogels have been plagued by poor electrical responsivity.

Accordingly, there is need in the art for electrically responsive hydrogels with enhanced electrical response.

SUMMARY

Provided herein are electro-responsive cryogels. The cryogels provided herein have enhanced and rapid electrical collapse (in tens of seconds) compared to electro-responsive hydrogels currently known in the art. Further, the cryogels described herein show extensive electrical collapse (down to less than 5% of their original area, high quality of electrical collapse (cryogels remain intact), precisely timed and organized control through inexpensive and unsophisticated means. Moreover, the cryogels described herein are composed of biologically friendly materials while retaining highly electro-responsive profiles, and are capable of comprising and delivering drugs in a triggered and stimulus-proportioned manner.

Generally, the electro-responsive cryogel described herein comprises a matrix material comprising cross-linked charged monomers and having interconnected macropores therein. In some embodiments, the charged monomers are acrylic acid. The charged monomers in the cryogel can be cross-linked using cross-linking monomers. In some embodiments, the cross-linker molecules are N,N'-methylenebis-acrylamide (BA) or polyethyleneglycol di(meth)acrylate (PEG-DM).

In some embodiments, the cryogel further comprises uncharged monomers. The uncharged monomers can be cross-linked with the charged monomers, directly or by the cross-linker monomers. In some embodiments, the uncharged monomers are acrylamide.

The cryogel can be prepared using cryogelation. Generally, an aqueous solution of charged monomers and cross-linker monomers is polymerized at a below the freezing temperature of aqueous solvent.

In some embodiments, the cryogel further comprises a therapeutic agents or a detectable molecule.

BRIEF DESCRIPTION OF THE DRAWINGS

FIG. 1A shows X-ray microtomography (μCT) three-dimensional reconstructions comparing the porosity of select polyelectrolytic hydrogels (top row) and two-dimensional slices from μCT reconstructions highlighting cross-sectional porosity (bottom row). On the top row, reconstructed volumes are presented. On the bottom row, 2 dimensional images are provided where pore space is represented in black while the gel walls are white. Each gel is crosslinked using 0.1% wt BA. FIG. 1B shows pore interconnectivity for select polyelectrolytic gels formed at room temperature compared to cryogels formed at −20° C. FIG. 1C shows Young's moduli for gels formed at room temperature compared to cryogels. FIG. 1D shows photographs of a cryogel collapsing under 50 V stimulation (top row) compared to the mechanical failure of room-temperature-gelled sample subjected to the same electric field (bottom row). A plot of the diameter of these gels over time and an 'x' marking the time of fracture for the room-temperature-gelled sample (bottom graph). FIG. 1E shows SEM images of the cryogels, highlighting their pore structure before (top) and after (bottom) electrical collapse. In FIGS. 1B and 1C values represent mean and standard deviation (N=6). *, , and * indicate $p \leq 0.05$, 0.01, and 0.001, respectively.

FIG. 2A shows cryogel diameter plotted versus time for samples composed of varying amounts of anionic (at pH>4.35) AAc crosslinked with 0.1% wt BA at the indicated weight percentages of AAc. Gels were exposed to 50V for 10 min. Gel diameter versus time for full duration of experiment (rightmost graph) with a zoom-in (graph at left) highlighting gel diameter during the first 3 minutes of the experiment. The horizontal black line represents the half-diameter of the gel (i.e., half way between the maximum gel diameter of 19 mm and its minimum possible diameter of 4.5 mm). The time it takes gels to reach half diameter (FIG. 2B) and the diameter of the gels after 10 minutes (FIG. 2C) are plotted for cryogels ranging from 4% wt to 12% wt AAc. FIG. 2D shows the time to reach half diameter (left graph) and diameters after 10 min (right graph) are plotted for gels composed of both anionic AAc and neutral AAm. Bar color indicates the amount of AAc present in % wt as indicated by the legend. All gels were crosslinked using 0.1% wt BA and initial diameter of all gels was 19 mm. All values represent mean and standard deviation (N=3). * and ** indicate $p \le 0.05$ and 0.01, respectively. In FIG. 2D, asterisks signify that the time to reach 50% diameter or the diameter after 10 minute are statistically ($p \le 0.05$) less than the corresponding values of the 11% wt (0% wt AAm) gels in FIGS. 2B and 2C.

FIGS. 3A-3C show crosslinking density and applied voltage have a deterministic effect on electrical collapse, allowing dynamic arrays of gels that are individually addressed. FIG. 3A shows cryogel diameter plotted versus time for gels composed of 4% wt AAc, 4% wt AAm and crosslinked with varying concentrations of BA (from 0.01% wt to 1% wt) over the course of 10 minutes (rightmost graph). A zoom-in to the first 3 minutes of voltage exposure is provided at left. Curve color indicates BA concentration as is indicated in the legend. Gels are exposed to 50 V in deionized water. FIG. 3B shows cryogel diameter plotted versus time for gels again composed of 4% wt AAc, 4% wt AAm, crosslinked using 0.1% wt BA when exposed to the indicated voltages. A zoom-in is provided at left to highlight the first 3 minutes of collapse. FIG. 1C shows an array of 4% wt AAc, 4% wt AAm cryogels, crosslinked with 0.1% wt BA, created to demonstrate the ability to easily control individual gel collapse. In the top row, select cryogels that encapsulate red polystyrene pigment beads are collapsed to create the image of the letter "H," centered in the array. Select gel collapse was stimulated by only addressing voltages (50 V for 3 min) to those particular gels. In the bottom row, similar cryogels that encapsulate red-, yellow-, and blue-pigment beads are used to transition from a blue, red and yellow optical state to one that is primarily blue. In FIGS. 3A and 3C values represent mean and standard deviation (N=3).

FIG. 4A, polyelectrolytic cryogels are created using more biocompatible materials: AAc cryogels crosslinked using PEG-DM. Snapshots of a 9% wt AAc cryogel crosslinked with 1% wt PEG-DM (labeled with rhodamine) are shown at the indicated times when exposed to 50 V in deionized water, demonstrating successful collapse. The rate (FIG. 4B) and extent (FIG. 4C) of these cryogels' electrical collapses are plotted versus the amount of AAc and PEG-DM used to construct the cryogel. AAc concentrations ranging from 4% wt-11% wt are coded indicated in the legend. Missing bars represent conditions that had insufficient polymeric concentrations to form gels. ‡ indicate gels that present a local minimum in collapse rate as AAc in increased. FIG. 4D, 9% wt AAc cryogels, crosslinked with 1% wt PEG-DM were loaded with miotoxantrone (i) and used to demonstrate voltage-triggered release of this model drug when submerged in PBS (ii-v). Cumulative mitoxantrone release resulting from 10-minute, 2.5 V pulses spaced 24 hours apart is plotted vs. time (vi). Drug release rates are indicated in black text along each segment of the curve. FIG. 4E, a10-cryogel array is formed where each cryogel can independently be stimulated by 2.5 V (top picture). Cryogels contain one of two drugs: auramine O and mitoxantrone. In the top row, gels containing auramine O are connected to voltage $v_1$. In the bottom row, two cryogels containing mitoxantrone are connected to $v_2$ and the other three are connected to $v_3$. Cumulative release profiles for auramine O (left y-axis) and mitoxantrone (right y-axis) when a sequence of voltages is turned on/off (bottom graph). In FIGS. 4B-4E, values represent mean and standard deviation ((FIG. 4B) and (FIG. 4C), N=3; (FIG. 4D) and (FIG. 4E), N=4).

FIG. 5A is a schematic representation of synthesis of cryogels. A pre-gel solution is prepared by mixing monomers and/or polymers, freezing that solution during the polymerization process to generate ice crystals, and thawing the gel after polymerization, leaving interconnected voids (or pores) where the ice crystals once existed. FIG. 5B shows a schematic of the experimental apparatus to illustrate placement of the gel (top), the directionality of the electric field used to stimulate the gels and the direction of expected gel collapse (bottom). FIG. 5C is a photograph of the experimental apparatus (left) and snapshots of a gel, colored with encapsulated polystyrene beads, collapsing under electrical stimulation (right from top to bottom). Electrical responsivity tests can take place with gels submerged in different solutions.

FIG. 6A, shows comparison of the collapse of 4% wt AAc, 4% wt AAm, 0.1% wt BA gels when exposed (bottom curve) and not exposed (top curve) to 50 V (part i) and pH of medium (part ii) measured before (t=0 s) and after (t=600 s) experiments where 0 or 50 V was used, with and without gels present. FIG. 6B shows collapse over time for gels exposed to 50 V (bottom curve) or 0 V (top curve) when pH was changed from 7 to 13 at time t=0 through the addition of NaOH. FIG. 6C shows collapse over time for gels exposed to 50 V (bottom curve) or 0 V (top curve) when the solution was changed to 100 mM NaCl at time t=0 through the addition of NaCl. In FIGS. 6A-6C, gel diameter vs time values represent mean and standard deviation (N=3). In FIG. 6A, part ii, N=4 and statistical significance was calculated comparing data at 600 s to data at 0 s. *** indicates $p \le 0.001$.

DETAILED DESCRIPTION OF EXEMPLARY EMBODIMENTS

Figure 1A:
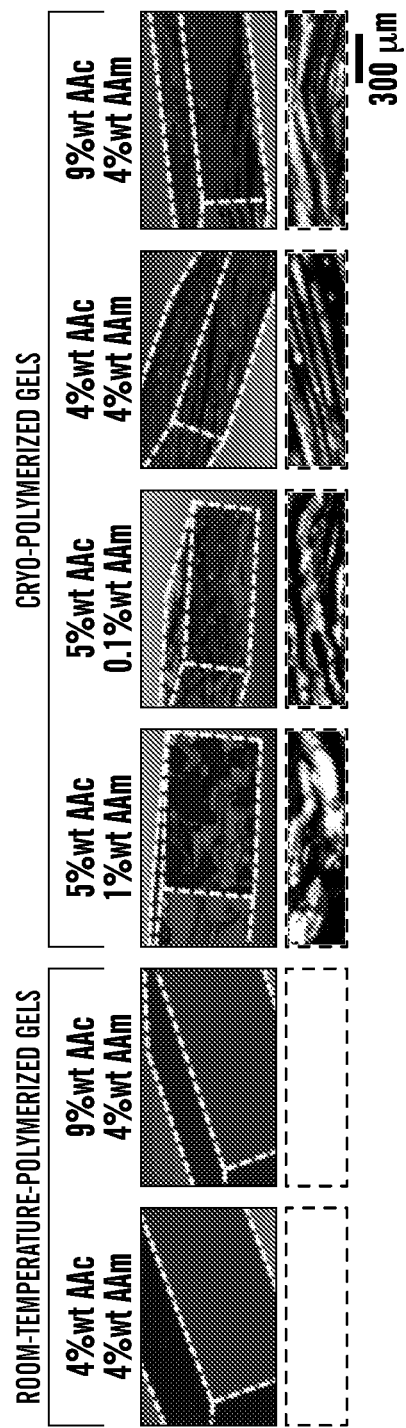
FIGS. 1A-1E show macroporous gels exhibit increased porosity and are able to collapse more rapidly and to a greater extent than their room-temperature-gelled counterparts.

In one aspect provided herein is an electro-responsive cryogel. As used herein, an electro-responsive cryogel refers to a hydrogel that can vary its porosity, pore size, pore connectivity, swelling agent concentration, and/or specific volume in response to an electrical stimulus. The changes in porosity, pore size, pore connectivity, swelling agent concentration, and/or specific volume are preferably reversible (i.e., porosity, pore size, pore connectivity, swelling agent concentration, and/or specific volume detectably increases or decreases upon application of the stimulus, and then reverts to its original value, e.g., within 15%, 10%, 7.5%, 5%, 2%, 1%, 0.5%, or less of the original value, when the stimulus is discontinued). However, it will be recognized that in some applications, reversibility of one or more of porosity, pore size, pore connectivity, swelling agent concentration, and/or specific volume is not essential. The change in specific volume is also referred to as a volume phase transition herein.

Generally, the electro-responsive cryogel described herein is a macroporous hydrogel, i.e., the cryogel comprises a matrix having interconnected macropores therein. Without wishing to be bound by a theory, an interconnected pore structure allows for more efficient syneresis of water and egression of ions from the hydrogel, thus providing greater responsivity. Additionally, apparent reductions in gel volume can be directly related to the volumetric collapse of macropores and not large-scale polymer rearrangement and/or polymer translocation per se. This can allow for more rapid reductions in gel volume while preserving the structural integrity of the gel.

As used herein, the term "hydrogel" refers to a three-dimensional polymeric structure that is insoluble in water but which is capable of absorbing and retaining large quantities of water to form a stable, often soft and pliable, structure. In some embodiments, water can penetrate in between the polymer chains of the polymer network, subsequently causing swelling and the formation of a hydrogel. In general, hydrogels can be superabsorbent.

In addition to the macropores, the cryogel can also comprise micropores. Generally, micropores are pores having a pore size on the order of about 50 Angstroms or less, while macropores are pores having a pore size on the order of about 100 Angstroms or greater. As used herein, the term "pore size" refers to a diameter or an effective diameter of the cross-sections of the pores. The term "pore size" can also refer to an average diameter or an average effective diameter of the cross-sections of the pores, based on the measurements of a plurality of pores. The effective diameter of a cross-section that is not circular equals the diameter of a circular cross-section that has the same cross-sectional area as that of the non-circular cross-section. In some embodiments, the cryogel can be swollen when the cryogel is hydrated. The sizes of the pores size can then change depending on the water content in the hydrogel. The pores can be filled with a fluid such as water or air. It will be understood by one of ordinary skill in the art that pores can exhibit a distribution of sizes around the indicated "size." Unless otherwise stated, the term "size" as used herein refers to the mode of a size distribution of pores, i.e., the value that occurs most frequently in the size distribution.

Generally, pore size of a macropore is such as to allow free flow of swelling agent and/or a solvent through the pores. Typically, pore diameters of cryogels described herein can range from about 0.01 µm to 5000 µm. In some embodiments, the cryogel comprises pores having mean pore diameter in range from about 10 µm to 1000 µm. In some embodiments, the cryogel comprises pores having mean pore diameter of 100-750 µm. In some embodiment, the cryogel comprises pores having mean pore diameter of 250-700 µm.

The pores can be substantially round cross-section or opening. What is meant by "substantially round" is that the ratio of the lengths of the longest to the shortest perpendicular axes of the pore cross-section is less than or equal to about 1.5. Substantially round does not require a line of symmetry. In some embodiments, the ratio of lengths between the longest and shortest axes of the pore cross-section is less than or equal to about 1.5, less than or equal to about 1.45, less than or equal to about 1.4, less than or equal to about 1.35, less than or equal to about 1.30, less than or equal to about 1.25, less than or equal to about 1.20, less than or equal to about 1.15 less than or equal to about 1.1.

The cryogels disclosed herein have a high degree of pore interconnectivity. For example, the cryogels described herein have pore interconnectivity that is at least 5%, 10%, 15%, 20%, 25%, 30%, 40%, 50%, 60%, 70%, 80%, 90%, 95%, 1-fold, 1.5, 2-fold, 2.5 fold or higher than the pore interconnectivity of a reference or control gel. In some embodiments, the cryogel has a pore interconnectivity of at least 20%, 25%, 30%, 40%, 50%, 60%, 70%, 80%, 90%, 95%, or higher. In some embodiments, the cryogel has a pore interconnectivity of from between about 25% to about 50%, from about 30% to about 45%, or from about 35% to about 40%.

The cryogels disclosed herein generally have high porosity. As used herein, the term "porosity" means the fractional volume (dimension-less) of the gel that is composed of open space, e.g., pores or other openings. See for example, Coulson J. M., et al., Chemical Engineering, 1978, volume 2, $3^{rd}$ Edition, Pergamon Press, 1978, page 126). Generally, in the absence of an external signal, porosity of the cryogel can range from 0.5 to 0.99. Preferably porosity is in the range of from about 0.75 to about 0.99, more preferably from about 0.8 to about 0.95. Preferably, porosity of the cryogel is at least 0.75, more preferably at least 0.8, and most preferably at least 0.9.

Several methods can be employed to measure porosity, including, direct methods (e.g. determining the bulk volume of the porous sample, and then determining the volume of the skeletal material with no pores (pore volume=total volume−material volume), optical methods (e.g., determining the area of the material versus the area of the pores visible under the microscope, where the areal and volumetric porosities are equal for porous media with random structure), imbibition methods (e.g., immersion of the porous sample, under vacuum, in a fluid that preferentially wets the pores), water saturation method (e.g., pore volume=total volume of water−volume of water left after soaking), water evaporation method (e.g., pore volume in cubic centimeters=weight of saturated sample in grams−weight of dried sample in grams), and gas expansion methods. Methods for measuring porosity of a sample are described in Glasbey, C. A. Horgan, G. W. and Darbyshire, J. F., *J. Soil Sci.* 1991, 42, 479-486, contents of which are herein incorporated by reference in their entirety.

Generally, the cryogels disclosed herein have an elastic modulus that is relatively lower than a reference or control gel. For example, the elastic module of the cryogel described herein can be at least 5%, 10%, 15%, 20%, 25%, 30%, 40%, 50%, 60%, 70%, 80%, 90%, 95%, 1-fold, 1.5, 2-fold, 2.5 fold or lower than a reference or control gel. The reference or control gel can be a gel having the same constituents as the cryogel but without the macropores or interconnected pores. The reference or control gel can also be a gel having the same constituent as the cryogel but prepared at room temperature.

In some embodiments, the cryogel modulus can range between $10^{-3}$ and $10^8$ Pa. In some embodiments, the cryogel has an elastic modulus in the range between $10^{-3}$ and $10^5$ Pa. In some embodiments, the elastic modulus can be less than about 10 kPa, about 7.5 kPa, about 5 kPa, about 2.5 kPa, or about 1 kPa. In some embodiments, the elastic modulus can range from about 0.5 kPa to about 7.5 kPa.

As used herein, the term "elastic modulus" refers to an object or substance's tendency to be deformed elastically (i.e., non-permanently) when a force is applied to it. Generally, the elastic modulus of an object is defined as the slope of its stress-strain curve in the elastic deformation region. Specifying how stress and strain are to be measured, including directions, allows for many types of elastic moduli to be defined. Young's modulus (E) describes tensile elasticity, or the tendency of an object to deform along an axis when opposing forces are applied along that axis; it is defined as the ratio of tensile stress to tensile strain. It is often referred to simply as the elastic modulus. The shear modulus or modulus of rigidity (G or $\mu$) describes an object's tendency to shear (the deformation of shape at constant volume) when acted upon by opposing forces; it is defined as shear stress over shear strain. The shear modulus is part of the derivation of viscosity. The bulk modulus (K) describes volumetric elasticity, or the tendency of an object to deform in all directions when uniformly loaded in all directions; it is defined as volumetric stress over volumetric strain, and is the inverse of compressibility. The bulk modulus is an extension of Young's modulus to three dimensions. Three other elastic moduli are Poisson's ratio, Lamé's first parameter, and P-wave modulus.

The matrix of the cryogel can be composed of a matrix material which comprises charged monomers. As used herein, the term "charged monomer" refers to a molecule that carries a charge at neutral pH and is capable of undergoing polymerization. In some embodiments, the charged monomer has a negative charge at neutral pH. Generally, the charged monomer comprises at least one functional group that can undergo polymerization. For example, a monomer can comprise a double bond which allows the monomer to undergo polymerization by cationic addition polymerization or anionic addition polymerization. Exemplary charged monomers include, but are not limited to, acrylic acid, methacrylic acid, and derivatives thereof which are charged at neutral pH.

Without wishing to be bound by a theory, the following polymers/monomers, alginate, heparin, and charged proteins can also work as the matrix material. One aspect of the discovery is that one can exert an electrical force on the matrix by virtue of it being charged (positive or negative). This force usually results in gel failure. However, the inventors have discovered that if the gel macroporous, gel failure is reduced when an electrical force is applied.

In some embodiments, the cryogel can be composed of cross-linked material. For example, the cryogel can comprise cross-linker monomers which can cross-link the matrix material comprising the charged monomers. As used herein, the term "cross-linker monomer" refers to any molecule has a plurality of reactive groups that can undergo polymerization. Suitable crosslinking agents include compounds whose molecule has a plurality of reactive groups. Such molecular crosslinking agents can be N,N'-methylenebis-acrylamide (BA), polyethyleneglycol di(meth)acrylate (PEG-DM), divinylbenzene (DVB), ethylene glycol dimethacrylate, divinyl ketone, vinyl methacrylate, divinyl oxalate, and adipc acid dihydrzide (AAD).

Without wishing to be bound by a theory, degree of cross-linking in the cryogel can also affect its properties. Accordingly, the degree of cross-linking can range from 0% (i.e., no cross-linking) to 100% (i.e. all groups for available for cross-linking are used). In some embodiments, degree of cross-linking is in the range of from about 5% to about 95%, from about 10% to about 90%, from about 15% to about 80%, from about 20% to about 75%, or from about 25% to about 50%.

In some embodiments, degree of cross-linking is less than 5%. For example less than 4%, 3%, 2%, 1.5%, 1%, 0.75%, 0.5%, 0.25%, or 0.2%. In some embodiments, degree of cross-linking is at least 0.05%. the range of from about 5% to about 95%, from about 10% to about 90%, from about 15% to about 80%, from about 20% to about 75%, or from about 25% to about 50%.

Electrical response of the cryogel can be modulated by copolymerizing uncharged monomers in the cryogel. Accordingly, in some embodiments, matrix material further comprises uncharged monomers. As used herein, the term "uncharged monomer" refers to molecule that do not have a charge at neutral pH and is capable of undergoing polymerization. In many instances, uncharged monomers are derivatives of charged monomers wherein the charge has been blocked. In some embodiments, uncharged monomers can be selected from the group consisting of N-substituted and non-substituted acrylamides; N-substituted and non-substituted (meth)acrylamides; N-alkyl substituted N-vinylamides; Hydroxyalkyl (meth)acrylates; vinylacetate; alkylethers of vinyl alcohols; styrene and ring substituted styrene derivatives; vinyl monomers; and any combination thereof.

Examples of N-substituted and non-substituted (meth)acrylamides to be used in the preparation of the macroporous gels according to the invention are acrylamide, methacrylamide, N,N-diallyl acrylamide, N,N'-methylenebis-acrylamide, N,N'-methylene-bis-methacrylamide, N,N'hexamethylene-bis-acrylamide, N,N-diethylacrylamide, N-isopropylacrylamide, N-butyracrylamide, N-(2-hydroxypropyl)methacrylamide.

Examples of N-alkyl substituted N-vinylamides to be used in the preparation of the macroporous gels according to the invention are N-vinyl pyrrolidone, N-vinyl caprolactam, N-vinyl-N-methylacetamide, N-vinyl-N-ethylacetamide.

Examples of hydroxyalkyl (meth)acrylates to be used in the preparation of the macroporous gels according to the invention are poly(ethylene glycol)diacrylates, (ethylene glycol)dimethacrylate, 2-hydroxyethylmethacrylate, 2-hydroxypropyl-methacrylate, 2-hydroxyethylacrylate, 4-hydroxybutylmethacrylate.

Examples of alkyl ethers of vinyl alcohol to be used in the preparation of the macroporous gels according to the invention are vinyl methyl ether, vinyl ethyl ether, vinyl propyl ether, vinyl isopropyl ether, vinyl butyl ether.

Examples of ring substituted styrene derivatives to be used in the preparation of the macroporous gels according to the invention are 4-styrenesulfonic acid sodium salt, 4-chloro-mefhylstyrene, methylstyrene, 4-vinylbenzoic acid.

Examples of vinyl monomers to be used in the preparation of the macroporous gels according to the invention are 2-vinylpyridine, 4-vinylpyridine, N-vinylcarbazole, 1-vinylimidazole, vinylazalactone, N-vinylurea.

The salts of (meth)acrylic acid which can be used in the preparation of the macroporous gels according to the invention are primarily the Na, K and ammonium salts.

Amount of the various components can be chosen as to provide a cryogel with desired properties. For example, amount of the charged monomer in the cryogel can range from about 1% to about 90% by weight of the cryogel. In some embodiments, amount of the charged monomer in the cryogel can range from about 50% to about 100% by weight of the cryogel.

Without limitations, amount of cross-linker monomers can range from about 0.005% to about 10% by weight of the cryogel. In some embodiments, amount of the cross-linker monomers can range from about 0.005% to about 1% by weight of the cryogel.

When present, amount of the uncharged monomer can range from about 0.01% to about 50% by weight of the cryogel.

Ratio of various components of the cryogel can be chosen to provide a cryogel with the desired properties. For example, ratio of charged monomer to cross-linker monomer can range from about 100:1 to 1:1 by weight, volume, or mol. In some embodiments, ratio of charged monomer to cross-linker monomer can range from about 40:1 to 2:1. In some embodiments, ratio of charged monomer to cross-linker monomer is about 4:0.1, about 4:0.2, about 4:0.5, about 4:0.7, about 4:1, about 4:2, about 4:5, about 5:0.1, about 5:0.2, about 5:0.5, about 5:0.7, about 5:1, about 5:2, about 5:5, about 6:0.1, about 6:0.2, about 6:0.5, about 6:0.7, about 6:1, about 6:2, about 6:5, about 7:0.1, about 7:0.2, about 7:0.5, about 7:0.7, about 7:1, about 7:2, about 7:5, about 8:0.1, about 8:0.2, about 8:0.5, about 8:0.7, about 8:1, about 8:2, about 8:5, about 9:0.1, about 9:0.2, about 9:0.5, about 9:0.7, about 9:1, about 9:2, about 4:5, about 10:0.1, about 10:0.2, about 10:0.5, about 10:0.7, about 10:1, about 10:2, about 10:5, about 11:0.1, about 11:0.2, about 11:0.5, about 11:0.7, about 11:1, about 11:2, or about 11:5.

When present, ratio of charged monomer to uncharged monomer can range from about 100:1 to 1:100 by weight, volume, or mol. For example, ratio of charged monomer to uncharged monomer can range from about 50:1 to 1:50, about 50:1 or about 1:50. In some embodiments, ratio of charged monomer to uncharged monomer is about 50:1, about 5:1, about 9:4, or about 1:1. In some embodiments, ratio of charged monomer to uncharged monomer is about 4:0.1, about 4:0.5, about 4:1, about 4:1, about 4:2, about 4:4, 5:0.1, about 5:0.5, about 5:1, about 5:1, about 5:2, about 5:4, 6:0.1, about 6:0.5, about 6:1, about 6:1, about 6:2, about 6:4, 7:0.1, about 7:0.5, about 7:1, about 7:1, about 7:2, about 7:4, 8:0.1, about 8:0.5, about 8:1, about 8:1, about 8:2, about 8:4, 9:0.1, about 9:0.5, about 9:1, about 9:1, about 9:2, or about 9:4.

The inventors have discovered that gels having charged monomers in a higher amount (by weight, volume, or mole) than the uncharged monomers have better electrical responsivity. Accordingly, in some embodiments, amount of charged monomers is higher than the amount of the charged monomers.

The inventors have discovered inter alia that polymeric charge density of the cryogel can modulate the responsiveness of the cryogel to the electrical stimulus. For example, while charge is required for gels to respond electrically, more moderate charge densities (50/50 charged/uncharged monomer) performs best. Without wishing to be bound by a theory, this can be attributed to two possible phenomena: (i) utilization of more charged monomer increases the amount of counterions that need to be displaced before the gel can undergo volumetric collapse and (ii) an extremely high charge density along the polymer backbone results in more electrostatic repulsion between polymer chains, thereby impeding collapse. The polymeric charge density of the cryogel can be at least $0.005$ e $Da^{-1}$, $0.006$ e $Da^{-1}$, $0.007$ e $Da^{-1}$, $0.008$ e $Da^{-1}$, $0.008$ e $Da^{-1}$, $0.010$ e $Da^{-1}$, or higher. In some embodiments, the polymeric charge density of the cryogel can be from about $0.005$ e $Da^{-1}$ to about $0.01$ e $Da^{-1}$.

In some embodiments, in response to electrical stimulus, porosity, pore size, pore connectivity, swelling agent concentration, and/or specific volume changes by at least 10%, 15%, 20%, 25% 30%, 40%, 50%, 60%, 70%, 80%, 90%, 95%, 96%, 97%, 98%, 99% or more relative to the original value. In some embodiments, in response to to electrical stimulus, porosity, pore size, pore connectivity, swelling agent concentration, and/or specific volume changes by at least 70% or more relative to the original value. Preferably, the porosity, pore size, pore connectivity, swelling agent concentration, and/or specific volume decreases in response to the electrical stimulus. Further, the change in porosity, pore size, pore connectivity, swelling agent concentration, and/or specific volume, in response to the electrical stimulus, occurs within 24 hours, 18 hours, 12 hours, 6 hours, 5 hours, 4 hours, 3 hours, 2 hours, 1 hour, 55 minutes, 50 minutes, 4 minutes, 40 minutes, 35 minutes, 30 minutes, 25 minutes, 20 minutes, 15 minutes, 10 minutes, 5 minutes, 4 minutes, 3 minutes, 2 minutes, 1 minute, 55 seconds, 50 seconds, 45 seconds, 40 seconds, 35 seconds, 30 seconds, 25 seconds, 20 seconds, 15 seconds, or within 10 seconds of onset of application of the electrical stimulus.

Generally electrical stimulus of any voltage can be applied to induce a change in porosity, pore size, pore connectivity, swelling agent concentration, and/or specific volume of the cryogel. For example, the electrical stimulus can range from 1V to 500V. In some embodiments, the electrical stimulus can range from 5V to 250V. In one embodiment, the electrical stimulus can be about 2.5V, about 5V, about 10V, about 25V, about 100, or about 250V.

The cryogel can be swellable. The term "swellable" refers to cryogels that are substantially insoluble in a swelling agent and are capable of absorbing a substantial amount of the swelling agent, thereby increasing in volume when contacted with the swelling agent. As used herein, the term "swelling agent" refers to those compounds or substances which affect at least a degree of swelling. Typically, swelling agents is an aqueous solution or organic solvent, however swelling agent can also be a gas. In some embodiments, swelling agent is water or a physiological solution, e.g. phosphate buffer saline, or growth media.

In some embodiments, the cryogel comprises a swelling agent. In some embodiments, the cryogel can contain over 50% (w/v), over 60% (w/v), over 70% (w/v), over 80% v, over 90% (w/v), over 91% (w/v), over 92% (w/v), over 93% (w/v), over 94% v, over 95% (w/v), over 96% (w/v), over 97% v, over 98% (w/v), over 99% (w/v), or more of the swelling agent.

The term "swelling ratio" is used herein to mean weight of swelling agent in swollen hydrogel per the dried weight of the cryogel gel before swelling. For example, the swelling ratio can range from about 1 to about 10 gram of swelling agent to per gram of the total of charge, uncharged and cross-linking monomers in the cryogel. In some embodiments, the swelling ratio can be from about 1 to about 5 gram of swelling agent to per gram of the total of charge, uncharged and cross-linking monomers in the cryogel. In some embodiments, the swelling ratio can be about 1.25, about 1.5, about 1.75, about 2, about 2.25, about 2.5, about 2.75, about 3, about 3.25, about 3.5, about 3.75, about 4, about 4.25, about 4.5, about 4.75, or about 5 g of swelling agent to per gram of the total of charge, uncharged and cross-linking monomers in the cryogel.

The cryogels described herein can be prepared using cryogelation. Generally, an aqueous solution of charged monomers and cross-linker monomers is polymerized at a temperature below the freezing temperature of aqueous solvent in which the charged monomers and the cross-linker monomers are present. Without limitations, the macroporous cryogels can be homopolymers as well as copolymers. Further, monomers, monomer combinations and reaction initiator systems, when necessary, are chosen which can be expected from literature and practice to be sufficiently reactive to form polymers at the low temperatures contemplated for the preparation of cryogels disclosed herein.

Amount of the various components in the aqueous solution used for preparation of the cryogel can be chosen as to provide a cryogel with desired properties. For example, amount of the charged monomer in the aqueous solution can range from about 1% to about 50% by weight, volume, or mol. In some embodiments, amount of charged monomer in the aqueous solution ranges from 2% to 15%, e.g., 2%, 3%, 4%, 5%, 6%, 7%, 8%, 9%, 10%, 11%, 12%, 13%, 14,%, or 15%. In one embodiment, amount of charged monomer in the aqueous solution ranges from 4% to 11%. In another embodiment, amount of charged monomer in the aqueous solution is about 4% or about 9%.

Without limitations, amount of cross-linker monomers in the aqueous solution can range from about 0.005% to about 1% by weight, volume, or mol. For example, amount of cross-linker monomers in the aqueous solution can range from about 0.01% to about 2%. In some embodiments, amount of cross-linker monomers in the aqueous solution is about 0.01%, about 0.05%, about 0.1%, about 0.5% or about 1%. In some embodiments, amount of the cross-linker monomers in the aqueous solution ranges from about 0.1% to about 5%. In some embodiments, amount of cross-linker monomers in the aqueous solution is about 0.1%, about 0.2%, about 0.5%, about 0.7%, about 1%, about 2%, or about 5%.

When present, amount of the uncharged monomer in the aqueous solution can range from about 0.01% to about 50% by weight, volume, or mol. In some embodiments, amount of uncharged monomer in the aqueous solution ranges from 0.05% to 5%, e.g., 0.5%, 0.1%, 1%, 2%, 3%, 4%, or 5%. In one embodiment, amount of the uncharged monomer in the aqueous solution is about 0.1%, about 1%, or about 4%.

Ratio of various components of the cryogel in the aqueous solution can be chosen to provide a cryogel with the desired properties. For example, ratio of charged monomer to cross-linker monomer in the aqueous solution can range from about 100:1 to 1:1 by weight, volume, or mol. In some embodiments, ratio of charged monomer to cross-linker monomer in the aqueous solution can range from about 40:1 to 2:1. In some embodiments, ratio of charged monomer to cross-linker monomer in the aqueous solution is about 4:0.1, about 4:0.2, about 4:0.5, about 4:0.7, about 4:1, about 4:2, about 4:5, about 5:0.1, about 5:0.2, about 5:0.5, about 5:0.7, about 5:1, about 5:2, about 5:5, about 6:0.1, about 6:0.2, about 6:0.5, about 6:0.7, about 6:1, about 6:2, about 6:5, about 7:0.1, about 7:0.2, about 7:0.5, about 7:0.7, about 7:1, about 7:2, about 7:5, about 8:0.1, about 8:0.2, about 8:0.5, about 8:0.7, about 8:1, about 8:2, about 8:5, about 9:0.1, about 9:0.2, about 9:0.5, about 9:0.7, about 9:1, about 9:2, about 4:5, about 10:0.1, about 10:0.2, about 10:0.5, about 10:0.7, about 10:1, about 10:2, about 10:5, about 11:0.1, about 11:0.2, about 11:0.5, about 11:0.7, about 11:1, about 11:2, or about 11:5.

When present, ratio of charged monomer to uncharged monomer in the aqueous solution can range from about 100:1 to 1:100 by weight, volume, or mol. For example, ratio of charged monomer to uncharged monomer in the aqueous solution can range from about 50:1 to 1:50, about 50:1 or about 1:50. In some embodiments, ratio of charged monomer to uncharged monomer is about 50:1, about 5:1, about 9:4, or about 1:1.

In some embodiments, ratio of charged monomer to uncharged monomer in the aqueous solution is about 4:0.1, about 4:0.5, about 4:1, about 4:1, about 4:2, about 4:4, 5:0.1, about 5:0.5, about 5:1, about 5:1, about 5:2, about 5:4, 6:0.1, about 6:0.5, about 6:1, about 6:1, about 6:2, about 6:4, 7:0.1, about 7:0.5, about 7:1, about 7:1, about 7:2, about 7:4, 8:0.1, about 8:0.5, about 8:1, about 8:1, about 8:2, about 8:4, 9:0.1, about 9:0.5, about 9:1, about 9:1, about 9:2, or about 9:4.

Initiator systems conventionally used in connection with the polymerization of monomers or combinations of monomers described herein are used when necessary or desired. For example, cross-linking can be performed with photo-crosslinking methods. Only one or a combination of two or more photoinitiators can be used. Photoinitiators produce reactive free radical species that initiate the crosslinking and/or polymerization of monomers upon exposure to light. Any photoinitiator can be used in the crosslinking and/or polymerization reaction. In some other embodiments, an initiator of a cationic or anionic crosslinking and/or polymerization process can be used.

In general, cross-linking initiators are utilized at concentrations ranging between approximately 0.005% w/v and 5.0% w/v. For example, initiators can be utilized at concentrations of about 0.005% w/v, about 0.01% w/v, about 0.025% w/v, about 0.05% w/v, about 0.075% w/v, about 0.1% w/w, about 0.125% w/v, about 0.25% w/v, about 0.5% w/v, about 0.75% w/v, about 1% w/v, about 1.125% w/v, about 1.25% w/v, about 1.5% w/v, about 1.75% w/v, about 2% w/v, about 2.125% w/v, about 2.25% w/v, about 2.5% w/v, about 2.75% w/v, about 3% w/v, about 3.125% w/v, about 3.25% w/v, about 3.5% w/v, about 3.75% w/v, about 4% w/v, about 4.125% w/v, about 4.25% w/v, about 4.5% w/v, about 4.75% w/v, about 5% w/v or higher.

The solvent or solvent system used for cryopolymerization is selected from the group consisting of water and mixtures of water and water-miscible organic solvents. Preferably, the solvent to be used for the cryopolymerization is water alone but water in admixture with a minor amount of one or more water-miscible organic solvents, such as methanol, ethanol, dioxane, acetone, dimethyl sulfoxide, N,N-dimethylformamide and acetonitrile may also be contemplated.

The temperature to which polymerization is carried out depends on the freezing point of the solvent or solvent system used in each specific case. Generally, the polymerization temperature should generally be at least 5° C., 15° C., 20° C., 25° C., 30° C., 35° C., 40° C., or below the freezing point of the solvent or solvent system. For instance, in case of water as the solvent, freezing is generally carried out to a temperature within the range of from −5° C. to −40° C., preferably from −10° C. to −30° C. In one embodiment, polymerization is carried out a temperature of about −20° C.

After formation, the cryogel can be washed with appropriate liquids (e.g. water, buffers, surfactant-containing solutions, organic solvents, mixtures of organic solvents with water or with each other) to remove non-polymerized impurities. Thus, the cryogel can be substantially free of non-polymerized monomers.

In some embodiments, the cryogel further comprises a compound selected from the group consisting of small organic or inorganic molecules; saccharines; monosaccharides; disaccharides; trisaccharides; oligosaccharides; polysaccharides; peptides; proteins, peptide analogs and derivatives; peptidomimetics; antibodies (polyclonal and monoclonal); antigen binding fragments of antibodies; nucleic acids, e.g., oligonucleotides, antisense oligonucleotides, siRNAs, shRNAs, ribozymes, aptamers, microRNAs, pre-microRNAs, plasmid DNA (e.g. condensed plasmid DNA), modified RNA, etc. . . . ; nucleic acid analogs and derivatives; an extract made from biological materials such as bacteria, plants, fungi, or animal cells; animal tissues; naturally occurring or synthetic compositions; and any combinations thereof.

As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight of less than 5000 Daltons (5 kD), preferably less than 3 kD, still more preferably less than 2 kD, and most preferably less than 1 kD. In some cases it is preferred that a small molecule have a molecular mass equal to or less than 700 Daltons.

As used herein, the term "peptide" is used in its broadest sense to refer to compounds containing amino acids, amino acid equivalents or other non-amino groups, while still retaining the desired functional activity of a peptide. Peptide equivalents can differ from conventional peptides by the replacement of one or more amino acids with related organic acids (such as PABA), amino acids or the like or the substitution or modification of side chains or functional groups. The peptides can be linear or cyclic. A peptide can be modified to include one or more of D-amino acids, beta-amino acids, chemically modified amino acids, naturally occurring non-proteogenic amino acids, rare amino acids, and chemically synthesized compounds that have properties known in the art to be characteristic of an amino acid.

As used herein, the term "nucleic acid" or "oligonucleotide" or grammatical equivalents herein means at least two nucleotides, including analogs or derivatives thereof, that are covalently linked together. Exemplary oligonucleotides include, but are not limited to, single-stranded and double-stranded siRNAs and other RNA interference reagents (RNAi agents or iRNA agents), shRNA (short hairpin RNAs), antisense oligonucleotides, aptamers, ribozymes, and microRNAs (miRNAs). The nucleic acids can be single stranded or double stranded. The nucleic acid can be DNA, RNA or a hybrid, where the nucleic acid contains any combination of deoxyribo- and ribo-nucleotides, and any combination of uracil, adenine, thymine, cytosine and guanine.

The nucleic acid can comprise one or more nucleic acid modifications known in the art. For example, the nucleic acids can comprise one or more backbone modifications, e.g., phosphoramide (Beaucage et al., Tetrahedron 49(10): 1925 (1993) and references therein; Letsinger, J. Org. Chem. 35:3800 (1970)), phosphorothioate, phosphorodithioate, O-methylphophoroamidite linkages (see Eckstein, Oligonucleotides and Analogues: A Practical Approach, Oxford University Press), or peptide nucleic acid linkages (see Egholm, J. Am. Chem. Soc. 114:1895 (1992); Meier et al., Chem. Int. Ed. Engl. 31:1008 (1992); and Nielsen, Nature, 365:566 (1993), content of all of which is herein incorporated by reference. The nucleic acids can also include modifications to nucleobase and/or sugar moieties of nucleotides. Exemplary sugar modifications at the sugar moiety include replacement of 2'-OH with halogens (e.g., fluoro), O-methyl, O-methoxyethyl, $NH_2$, SH and S-methyl.

As used herein, the term "polysaccharide" refers to macromolecular carbohydrates whose molecule consists of a large number of monosaccharide molecules which are joined to one another by glycosidic linkage. The term polysaccharide is also intended to embrace an oligosaccharide. The polysaccharide can be homopolysaccharides or heteropolysaccharides. Whereas the homopolysaccharides contain only one kind of unit, the heteropolysaccharides consist of monomer units of different kinds.

In some embodiments, the cryogel comprises a bioactive agent. As used herein, "bioactive agents" refer to synthetic or naturally occurring materials that that have a biological effect on a biological cell, tissue or organ. In some embodiments, the bioactive agent can be a biological material, for example, extracellular matrix materials such as fibronectin, vitronection, and laminin, cytokines, growth factors and differentiation factors, nucleic acids, proteins, peptides, antibodies, and cells.

Suitable growth factors and cytokines include, but are not limited to, stem cell factor (SCF), granulocyte-colony stimulating factor (G-CSF), granulocyte-macrophage stimulating factor (GM-CSF), stromal cell-derived factor-1, steel factor, VEGF, TGFβ, platelet derived growth factor (PDGF), angiopoeitins (Ang), epidermal growth factor (EGF), bFGF, HNF, NGF, bone morphogenic protein (BMP), fibroblast growth factor (FGF), hepatocye growth factor, insulin-like growth factor (IGF-1), interleukin (IL)-3, IL-1α, IL-1β, IL-6, IL-7, IL-8, IL-11, and IL-13, colony-stimulating factors, thrombopoietin, erythropoietin, fit3-ligand, and tumor necrosis factor α (TNFα). Other examples are described in Dijke et al., "Growth Factors for Wound Healing", Bio/Technology, 7:793-798 (1989); Mulder G D, Haberer P A, Jeter K F, eds. Clinicians' Pocket Guide to Chronic Wound Repair. 4th ed. Springhouse, P A: Springhouse Corporation; 1998:85; Ziegler T. R., Pierce, G. F., and Herndon, D. N., 1997, International Symposium on Growth Factors and Wound Healing: Basic Science & Potential Clinical Applications (Boston, 1995, Serono Symposia USA), Publisher: Springer Verlag.

In some embodiments, suitable bioactive agents include, but are not limited to, therapeutic agents. As used herein, the term "therapeutic agent" refers to a substance used in the diagnosis, treatment, or prevention of a disease. Any therapeutic agent known to those of ordinary skill in the art to be of benefit in the diagnosis, treatment or prevention of a disease is contemplated as a therapeutic agent in the context of the present invention. Therapeutic agents include pharmaceutically active compounds, hormones, growth factors, enzymes, DNA, plasmid DNA, RNA, siRNA, antisense oligonucleotides, modified RNA, viruses, proteins, lipids, pro-inflammatory molecules, polyclonal antibodies, monoclonal antibodies, antibiotics, anti-inflammatory agents, anti-sense nucleotides and transforming nucleic acids or combinations thereof. Any of the therapeutic agents can be combined to the extent such combination is biologically compatible.

Exemplary therapeutic agents include, but are not limited to, those found in *Harrison's Principles of Internal Medicine*, 13th Edition, Eds. T. R. Harrison et al. McGraw-Hill N.Y., NY; Physicians' Desk Reference, 50th Edition, 1997, Oradell N.J., Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete contents of all of which are incorporated herein by reference.

Examples of therapeutic agents which can be incorporated in the cryogel, include, but are not limited to, narcotic analgesic drugs; salts of gold; corticosteroids; hormones; antimalarial drugs; indole derivatives; pharmaceuticals for arthritis treatment; antibiotics, including Tetracyclines, Penicillin, Streptomycin and Aureomycin; antihelmintic and canine distemper drugs, applied to domestic animals and large cattle, such, as, for example, phenothiazine; drugs based on sulfur, such, as sulfioxazole; antitumor drugs; pharmaceuticals supervising addictions, such as agents controlling alcohol addiction and agents controlling tobacco addiction; antagonists of drug addiction, such, as methadone; weight controlling drugs; thyroid gland controlling drugs; analgesics; drugs controlling fertilization or contraception hormones; amphetamines; antihypertensive drugs; antiinflammatories agents; antitussives; sedatives; neuromuscular relaxants; antiepileptic drugs; antidepressants; antidisrhythmic drugs; vasodilating drugs; antihypertensive diuretics; antidiabetic agents; anticoagulants; antituberculous agents; antipsychotic agents; hormones and peptides. It is understood that above list is not full and simply represents the wide diversification of therapeutic agents that may be included in the compositions. In some embodiments, therapeutic agent is Mitoxantrone, peptide, polyclonal antibody, monoclonal antibody, antigen binding fragment of an antibody, protein (e.g. VEGF) or plasmid DNA.

Therapeutic agents include the herein disclosed categories and specific examples. It is not intended that the category be limited by the specific examples. Those of ordinary skill in the art will recognize also numerous other compounds that fall within the categories and that are useful according to the present disclosure. Examples include a radiosensitizer, a steroid, a xanthine, a beta-2-agonist bronchodilator, an antiinflammatory agent, an analgesic agent, a calcium antagonist, an angiotensin-converting enzyme inhibitors, a beta-blocker, a centrally active alpha-agonist, an alpha-1-antagonist, an anticholinergic/antispasmodic agent, a vasopressin analogue, an antiarrhythmic agent, an antiparkinsonian agent, an antiangina/antihypertensive agent, an anticoagulant agent, an antiplatelet agent, a sedative, an ansiolytic agent, a peptidic agent, a biopolymeric agent, an antineoplastic agent, a laxative, an antidiarrheal agent, an antimicrobial agent, an antifingal agent, a vaccine, a protein, or a nucleic acid. In a further aspect, the pharmaceutically active agent can be coumarin, albumin, steroids such as betamethasone, dexamethasone, methylprednisolone, prednisolone, prednisone, triamcinolone, budesonide, hydrocortisone, and pharmaceutically acceptable hydrocortisone derivatives; xanthines such as theophylline and doxophylline; beta-2-agonist bronchodilators such as salbutamol, fenterol, clenbuterol, bambuterol, salmeterol, fenoterol; antiinflammatory agents, including antiasthmatic anti-inflammatory agents, antiarthritic antiinflammatory agents, and non-steroidal antiinflammatory agents, examples of which include but are not limited to sulfides, mesalamine, budesonide, salazopyrin, diclofenac, pharmaceutically acceptable diclofenac salts, nimesulide, naproxene, acetaminophen, ibuprofen, ketoprofen and piroxicam; analgesic agents such as salicylates; calcium channel blockers such as nifedipine, amlodipine, and nicardipine; angiotensin-converting enzyme inhibitors such as captopril, benazepril hydrochloride, fosinopril sodium, trandolapril, ramipril, lisinopril, enalapril, quinapril hydrochloride, and moexipril hydrochloride; beta-blockers (i.e., beta adrenergic blocking agents) such as sotalol hydrochloride, timolol maleate, esmolol hydrochloride, carteolol, propanolol hydrochloride, betaxolol hydrochloride, penbutolol sulfate, metoprolol tartrate, metoprolol succinate, acebutolol hydrochloride, atenolol, pindolol, and bisoprolol fumarate; centrally active alpha-2-agonists such as clonidine; alpha-1-antagonists such as doxazosin and prazosin; anticholinergic/antispasmodic agents such as dicyclomine hydrochloride, scopolamine hydrobromide, glycopyrrolate, clidinium bromide, flavoxate, and oxybutynin; vasopressin analogues such as vasopressin and desmopressin; antiarrhythmic agents such as quinidine, lidocaine, tocainide hydrochloride, mexiletine hydrochloride, digoxin, verapamil hydrochloride, propafenone hydrochloride, flecainide acetate, procainamide hydrochloride, moricizine hydrochloride, and disopyramide phosphate; antiparkinsonian agents, such as dopamine, L-Dopa/Carbidopa, selegiline, dihydroergocryptine, pergolide, lisuride, apomorphine, and bromocryptine; antiangina agents and antihypertensive agents such as isosorbide mononitrate, isosorbide dinitrate, propranolol, atenolol and verapamil; anticoagulant and antiplatelet agents such as Coumadin, warfarin, acetylsalicylic acid, and ticlopidine; sedatives such as benzodiazapines and barbiturates; ansiolytic agents such as lorazepam, bromazepam, and diazepam; peptidic and biopolymeric agents such as calcitonin, leuprolide and other LHRH agonists, hirudin, cyclosporin, insulin, somatostatin, protirelin, interferon, desmopressin, somatotropin, thymopentin, pidotimod, erythropoietin, interleukins, melatonin, granulocyte/macrophage-CSF, and heparin; antineoplastic agents such as etoposide, etoposide phosphate, cyclophosphamide, methotrexate, 5-fluorouracil, vincristine, doxorubicin, cisplatin, hydroxyurea, leucovorin calcium, tamoxifen, flutamide, asparaginase, altretamine, mitotane, and procarbazine hydrochloride; laxatives such as senna concentrate, casanthranol, bisacodyl, and sodium picosulphate; antidiarrheal agents such as difenoxine hydrochloride, loperamide hydrochloride, furazolidone, diphenoxylate hdyrochloride, and microorganisms; vaccines such as bacterial and viral vaccines; antimicrobial agents such as penicillins, cephalosporins, and macrolides, antifungal agents such as imidazolic and triazolic derivatives; and nucleic acids such as DNA sequences encoding for biological proteins, and antisense oligonucleotides.

Anti-cancer agents include alkylating agents, platinum agents, antimetabolites, topoisomerase inhibitors, antitumor antibiotics, antimitotic agents, aromatase inhibitors, thymidylate synthase inhibitors, DNA antagonists, farnesyltransferase inhibitors, pump inhibitors, histone acetyltransferase inhibitors, metalloproteinase inhibitors, ribonucleoside reductase inhibitors, TNF alpha agonists/antagonists, endothelinA receptor antagonists, retinoic acid receptor agonists, immuno-modulators, hormonal and anti-hormonal agents, photodynamic agents, and tyrosine kinase inhibitors.

Antibiotics include aminoglycosides (e.g., gentamicin, tobramycin, netilmicin, streptomycin, amikacin, neomycin), bacitracin, corbapenems (e.g., imipenem/cislastatin), cephalosporins, colistin, methenamine, monobactams (e.g., aztreonam), penicillins (e.g., penicillin G, penicillinV, methicillin, natcillin, oxacillin, cloxacillin, dicloxacillin, ampicillin, amoxicillin, carbenicillin, ticarcillin, piperacillin, mezlocillin, azlocillin), polymyxin B, quinolones, and vancomycin; and bacteriostatic agents such as chloramphenicol, clindanyan, macrolides (e.g., erythromycin, azithromycin, clarithromycin), lincomyan, nitrofurantoin, sulfonamides, tetracyclines (e.g., tetracycline, doxycycline, minocycline, demeclocyline), and trimethoprim. Also included are metronidazole, fluoroquinolones, and ritampin.

Enzyme inhibitors are substances which inhibit an enzymatic reaction. Examples of enzyme inhibitors include edrophonium chloride, N-methylphysostigmine, neostigmine bromide, physostigmine sulfate, tacrine, tacrine, 1-hydroxy maleate, iodotubercidin, p-bromotetramiisole, 10-(alpha-diethylaminopropionyl)-phenothiazine hydrochloride, calmidazolium chloride, hemicholinium-3,3,5-dinitrocatechol, diacylglycerol kinase inhibitor I, diacylglycerol kinase inhibitor II, 3-phenylpropargylamine, $N^\ominus$-monomethyl-Larginine acetate, carbidopa, 3-hydroxybenzylhydrazine, hydralazine, clorgyline, deprenyl, hydroxylamine, iproniazid phosphate, 6-MeO-tetrahydro-9H-pyrido-indole, nialamide, pargyline, quinacrine, semicarbazide, tranylcypromine, N,N-diethylaminoethyl-2,2-diphenylvalerate hydrochloride, 3-isobutyl-1-methylxanthne, papaverine, indomethacind, 2-cyclooctyl-2-hydroxyethylamine hydrochloride, 2,3-dichloro-a-methylbenzylamine (DCMB), 8,9-dichloro-2,3,4,5-tetrahydro-1H-2-benzazepine hydrochloride, p-amino glutethimide, p-aminoglutethimide tartrate, 3-iodotyrosine, alpha-methyltyrosine, acetazolamide, dichlorphenamide, 6-hydroxy-2-benzothiazolesulfonamide, and allopurinol.

Antihistamines include pyrilamine, chlorpheniramine, and tetrahydrazoline, among others.

Anti-inflammatory agents include corticosteroids, non-steroidal anti-inflammatory drugs (e.g., aspirin, phenylbutazone, indomethacin, sulindac, tolmetin, ibuprofen, piroxicam, and fenamates), acetaminophen, phenacetin, gold salts, chloroquine, D-Penicillamine, methotrexate colchicine, allopurinol, probenecid, and sulfinpyrazone.

Muscle relaxants include mephenesin, methocarbomal, cyclobenzaprine hydrochloride, trihexylphenidyl hydrochloride, levodopa/carbidopa, and biperiden.

Anti-spasmodics include atropine, scopolamine, oxyphenonium, and papaverine.

Analgesics include aspirin, phenybutazone, idomethacin, sulindac, tolmetic, ibuprofen, piroxicam, fenamates, acetaminophen, phenacetin, morphine sulfate, codeine sulfate, meperidine, nalorphine, opioids (e.g., codeine sulfate, fentanyl citrate, hydrocodone bitartrate, loperamide, morphine sulfate, noscapine, norcodeine, normorphine, thebaine, norbinaltorphimine, buprenorphine, chlomaltrexamine, funaltrexamione, nalbuphine, nalorphine, naloxone, naloxonazine, naltrexone, and naltrindole), procaine, lidocain, tetracaine and dibucaine.

Ophthalmic agents include sodium fluorescein, rose bengal, methacholine, adrenaline, cocaine, atropine, alpha-chymotrypsin, hyaluronidase, betaxalol, pilocarpine, timolol, timolol salts, and combinations thereof Prostaglandins are art recognized and are a class of naturally occurring chemically related, long-chain hydroxy fatty acids that have a variety of biological effects.

Anti-depressants are substances capable of preventing or relieving depression. Examples of anti-depressants include imipramine, amitriptyline, nortriptyline, protriptyline, desipramine, amoxapine, doxepin, maprotiline, tranylcypromine, phenelzine, and isocarboxazide.

Trophic factors are factors whose continued presence improves the viability or longevity of a cell. Trophic factors include, Without limitation, platelet-derived growth factor (PDGP), neutrophil-activating protein, monocyte chemoattractant protein, macrophage-inflammatory protein, platelet factor, platelet basic protein, and melanoma growth stimulating activity; epidermal growth factor, transforming growth factor (alpha), fibroblast growth factor, platelet-derived endothelial cell growth factor, insulin-like growth factor, glial derived growth neurotrophic factor, ciliary neurotrophic factor, nerve growth factor, bone growth/cartilage-inducing factor (alpha and beta), bone morphogenetic proteins, interleukins (e.g., interleukin inhibitors or interleukin receptors, including interleukin 1 through interleukin 10), interferons (e.g., interferon alpha, beta and gamma), hematopoietic factors, including erythropoietin, granulocyte colony stimulating factor, macrophage colony stimulating factor and granulocyte-macrophage colony stimulating factor; tumor necrosis factors, and transforming growth factors (beta), including beta-1, beta-2, beta-3, inhibin, and activin.

Hormones include estrogens (e.g., estradiol, estrone, estriol, diethylstibestrol, quinestrol, chlorotrianisene, ethinyl estradiol, mestranol), anti-estrogens (e.g., clomiphene, tamoxifen), progestins (e.g., medroxyprogesterone, norethindrone, hydroxyprogesterone, norgestrel), antiprogestin (mifepristone), androgens (e.g., testosterone cypionate, fluoxymesterone, danazol, testolactone), anti-androgens (e.g., cyproterone acetate, flutamide), thyroid hormones (e.g., triiodothyronne, thyroxine, propylthiouracil, methimazole, and iodixode), and pituitary hormones (e.g., corticotropin, sumutotropin, oxytocin, and vasopressin). Hormones are commonly employed in hormone replacement therapy and/or for purposes of birth control. Steroid hormones, such as prednisone, are also used as immunosuppressants and anti-inflammatories.

The biologically active agent can be an osteogenic protein. Accordingly, in some embodiments, the biologically active agent is desirably selected from the family of proteins known as the transforming growth factors beta (TGF-[3) superfamily of proteins, which includes the activins, inhibins and bone morphogenetic proteins (BMPs). Most preferably, the active agent includes at least one protein selected from the subclass of proteins known generally as BMPs, which have been disclosed to have osteogenic activity, and other growth and differentiation type activities. These BMPs include BMP proteins BMP-2, BMP-3, BMP-4, BMP5, BMP-6 and BMP-7, disclosed for instance in U.S. Pat. Nos. 5,108,922; 5,013,649; 5,116,738; 5,106,748; 5,187,076; and 5,141,905; BMP-8, disclosed in PCT publication WO91/18098; and BMP-9, disclosed in PCT publication WO93/00432, BMP-10, disclosed in PCT application WO94/26893; BMP-11, disclosed in PCT application WO94/26892, or BMP-12 or BMP-13, disclosed in PCT application WO 95/16035; BMP-14; BMP-15, disclosed in U.S. Pat. No. 5,635,372; or BMP-16, disclosed in U.S. Pat. No. 5,965,403. Other TGF-β proteins, which can be used include Vgr-2, Jones et al., Mol. Endocrinol. 611961 (1992), and any of the growth and differentiation factors (GDFs), including those described in PCT applications WO94/15965; WO94/15949; WO95/01801; WO95/01802; WO94/21681; WO94/15966; WO95/10539; WO96/01845; WO96/02559 and others. Also useful in the invention can be BIP, disclosed in WO94/01557; HP00269, disclosed in JP Publication number: 7-250688; and BMP-14 (also known as MP52, CDMP1, and GDF5), disclosed in PCT application WO93/16099. The disclosures of all of the above applications are incorporated herein by reference. Subsets of BMPs which can be used include BMP-2, BMP-3, BMP-3b, BMP-4, BMP-5, BMP-6, BMP-7, BMP-8, BMP-9, BMP-10, BMP-11, BMP-12, BMP-13, BMP-14, BMP-15, BMP-16, BMP-17, and BMP18. Other osteogenic agents known in the art can also be used, such as teriparatide (FORTEO™), CHRYSALIN®, prostaglandin E2, or LIM protein, among others.

The biologically active agent can be recombinantly produced, or purified from a protein composition. The active agent, if a TGF-β such as a BMP, or other dimeric protein, can be homodimeric, or can be heterodimeric with other BMPs (e.g., a heterodimer composed of one monomer each of BMP-2 and BMP-6) or With other members of the TGF-β superfamily, such as activins, inhibins and TGF-β1 (e.g., a heterodimer composed of one monomer each of a BMP and a related member of the TGF-β superfamily). Examples of such heterodimeric proteins are described for example in Published PCT Patent Application WO 93/09229, the content of which is incorporated herein by reference.

The active agent can further include additional agents such as the Hedgehog, Frazzled, Chordin, Noggin, Cerberus and Follistatin proteins. These families of proteins are generally described in Sasai et al., Cell 791779-790 (1994) (Chordin); PCT Patent Publication WO94/05800 (Noggin); and Fukui et al., Devel. Biol. 159: 1 31 (1993) (Follistatin). Hedgehog proteins are described in WO96/16668; WO96/17924; and WO95/18856. The Frazzled family of proteins is a recently discovered family of proteins With high homology to the extracellular binding domain of the receptor protein family known as Frizzled. The Frizzled family of genes and proteins is described in Wang et al., .1. Biol. Chem. 271:44684476 (1996). The active agent can also include other soluble receptors, such as the truncated soluble receptors disclosed in PCT patent publication WO95/07982. From the teaching of WO95/07982, one skilled in the art will recognize that truncated soluble receptors can be prepared for numerous other receptor proteins. The above publications are hereby incorporated by reference herein.

In some embodiments, the therapeutic agent is an art known therapeutic agent requiring relatively frequent dosing. Without wishing to be bound by a theory, a cryogel comprising two or more doses of a therapeutic agent requiring relatively frequent dosing can be administer to a subject, e.g., implanted in the subject. In some embodiments, amount of the therapeutic agent in the cryogel can be more than the amount generally recommended for one dosage of the same therapeutic agent administered for a particular indication. For example, if the recommended dosage of the therapeutic agent is X amount then the cryogel can comprise the therapeutic agent in an amount of about 1.25X, about 1.5X, about 1.75X, about 2X, about 2.5X, about 3X, about 4X, about 5X, about 6X, about 7X, about 8X, about 9X, about 10X or more.

Without wishing to be bound by a theory, this allows administering the therapeutic agent in the cryogel to obtain a therapeutic effect which is similar to one obtained with multiple administrations of the therapeutic agent administered without the cryogel. A therapeutically effective amount of the therapeutic agent can then be released by applying an electrical stimulus to the cryogel as needed. This can be used to administered the therapeutic agent once every 1-6 months (e.g., once every 1-2 months, once every 3-6 months) instead of the usually more frequent administration (e.g., 1-3 times or more a week) of the therapeutic agent. For example, the administration frequency for the therapeutic agent can be reduced by a factor of at least about 1/500, at least about 1/250, at least about 1/225, at least about 1/200, at least about 1/175, at least about 1/150, at least about 1/125, at least about 1/100, at least about 1/90. at least about 1/80, at least about 1/70, at least about 1/60, at least about 1/50, at least about 1/30, at least about 1/25, at least about 1/20, at least about 1/19, at least about 1/18, at least about 1/17, at least about 1/16, at least about 1/15, at least about 1/14, at least about 1/13, at least about 1/12, at least about 1/11, at least about 1/10, at least about 1/9, at least about 1/8, at least about 1/7, at least about 1/6, at least about 1/5, at least about 1/4, at least about 1/3, at least about 1/2, at least about 1/1.75, at least about 1/1.5, at least about 1/1.25, at least about 1/1.1, or more.

Without wishing to be bound by a theory, cryogel can also increase bioavailability of the encapsulated therapeutic agent. As used herein, the term "bioavailability" refers to the amount of a substance available at a given site of physiological activity after administration. Bioavailability of a given substance is affected by a number of factors including but not limited to degradation and absorption of that substance. Administered substances are subject to excretion prior to complete absorption, thereby decreasing bioavailability. In some embodiments, bioavailability of an encapsulated therapeutic agent can increase by at least 5%, at least 10%, at least 15%, at least 20%, at least 25%, at least 30%, at least 35%, at least 40%, at least 50%, at least 60%, at least 70%, at least 80%, at least 90%, at least 1-fold, at least 1.5-fold, at least 2-fold, at least 5-fold, at least 5-fold, at least 10-fold or more relative to the non-encapsulated therapeutic agent.

The amount of therapeutic agent distributed in the cryogel depends on various factors including, for example, specific agent; function which it should carry out; required period of time for release of a the agent; quantity to be administered. Generally, dosage of a therapeutic agent i.e. amount of therapeutic agent in the cryogel, is selected from the range about from 0.001% (w/w) up to 95% (w/w), preferably, from about 5% (w/w) to about 75% (w/w), and, most preferably, from about 10% (w/w) to about 60% (w/w).

In some embodiments, the bioactive material can be a cell, e.g. a biological cell. One way to incorporate cells into the cryogel is by reswelling a dried or partially dried cryogel in an aqueous solution comprising the cells to be incorporated. The aqueous solution can comprise from about $10^4$ to about $10^8$ cells/ml. In some embodiments, aqueous solution comprises from about $10^4$ to about $10^6$ cells/ml. In one preferred embodiment, aqueous solution comprises about $5 \times 10^5$ cells/ml.

In some embodiments, the composition comprises two or more different cell types. This can be accomplished by having two or more different cell types in aqueous solution used for swelling. When two or more different cell types are to be incorporated into the composition, total number of cells in the aqueous solution ranges from about $10^4$ to about $10^8$ cells/ml, about $10^4$ to about $10^6$ cells/ml, or about $10^5$ cells/ml.

Cells amenable to be incorporated into the composition include, but are not limited to, stem cells (embryonic stem cells, mesenchymal stem cells, bone-marrow derived stem cells and hematopoietic stem cells), chrondrocytes progenitor cells, pancreatic progenitor cells, myoblasts, fibroblasts, keratinocytes, neuronal cells, glial cells, astrocytes, preadipocytes, adipocytes, vascular endothelial cells, hair follicular stem cells, endothelial progenitor cells, mesenchymal cells, neural stem cells and smooth muscle progenitor cells.

In some embodiments, the cell is a genetically modified cell. A cell can be genetically modified to express and secrete a desired compound, e.g. a bioactive agent, a growth factor, differentiation factor, cytokines, and the like. Methods of genetically modifying cells for expressing and secreting compounds of interest are known in the art and easily adaptable by one of skill in the art.

Differentiated cells that have been reprogrammed into stem cells can also be used. For example, human skin cells reprogrammed into embryonic stem cells by the transduction of Oct3/4, Sox2, c-Myc and Klf4 (Junying Yu, et. al., *Science*, 2007, 318, 1917-1920 and Takahashi K. et. al., *Cell*, 2007, 131, 1-12).

Cells useful for incorporation into the composition can come from any source, e.g. a a mammal. For example the cell can be from a human, rat or mouse. Human cells include, but are not limited to, human cardiac myocytes-adult (HCMa), human dermal fibroblasts-fetal (HDF-f), human epidermal keratinocytes (HEK), human mesenchymal stem cells-bone marrow, human umbilical mesenchymal stem cells, human hair follicular inner root sheath cells, human umbilical vein endothelial cells (HUVEC), and human umbilical vein smooth muscle cells (HUVSMC), human endothelial progenitor cells, human myoblasts, human capillary endothelial cells, and human neural stem cells.

Exemplary rat and mouse cells include, but not limited to, RN-h (rat neurons-hippocampal), RN-c (rat neurons-cortical), RA (rat astrocytes), rat dorsal root ganglion cells, rat neuroprogenitor cells, mouse embryonic stem cells (mESC) mouse neural precursor cells, mouse pancreatic progenitor cells mouse mesenchymal cells and mouse endodermal cells.

In some embodiments, tissue culture cell lines can be used in the cryogels described herein. Examples of cell lines include, but not limited to, C166 cells (embryonic day 12 mouse yolk), C6 glioma Cell line, HL1 (cardiac muscle cell line), AML12 (nontransforming hepatocytes), HeLa cells (cervical cancer cell line) and Chinese Hamster Ovary cells (CHO cells).

An ordinary skill artisan in the art can locate, isolate and expand such cells. In addition, the basic principles of cell culture and methods of locating, isolation and expansion and preparing cells for tissue engineering are described in "Culture of Cells for Tissue Engineering" Editor(s): Gordana Vunjak-Novakovic, R. Ian Freshney, 2006 John Wiley & Sons, Inc., and Heath C. A., *Trends in Biotechnology*, 2000, 18, 17-19, content of both of which is herein incorporated by reference in its entirety.

The bioactive agent can be covalently linked to the cryogel through a linker. The linker can be a cleavable linker or non-cleavable linker, depending on the application. As used herein, a "cleavable linker" refers to linkers that are capable of cleavage under various conditions. Conditions suitable for cleavage can include, but are not limited to, pH, UV irradiation, enzymatic activity, temperature, hydrolysis, elimination and substitution reactions, redox reactions, and thermodynamic properties of the linkage. In many cases, the intended nature of the conjugation or coupling interaction, or the desired biological effect, will determine the choice of linker group.

In some embodiments, the bioactive agent is bound to the cryogel by a hydrolyzable bond. In some embodiments, the cell or the bioactive agent has a mean free path in the composition that is shorter than the mean free path of the cell or the bioactive agent in water.

In some embodiments, the matrix is functionalized with binding molecules that binds with a bioactive molecule. These binding molecules are also referred to as affinity molecules herein. The binding molecule can be bound covalently (directly or through a linker) or non-covalently to the matrix. The binding molecule can be selected such that it can bind to any part of bioactive molecule that is accessible.

As used herein, the term "binding molecule" or "affinity molecule" refers to any molecule that is capable of binding a bioactive molecule. Representative examples of affinity molecules include, but are not limited to, antibodies, antigens, lectins, proteins, peptides, nucleic acids (DNA, RNA, PNA and nucleic acids that are mixtures thereof or that include nucleotide derivatives or analogs); receptor molecules, such as the insulin receptor; ligands for receptors (e.g., insulin for the insulin receptor); and biological, chemical or other molecules that have affinity for another molecule, such as biotin and avidin. The binding molecules need not comprise an entire naturally occurring molecule but may consist of only a portion, fragment or subunit of a naturally or non-naturally occurring molecule, as for example the Fab fragment of an antibody.

Nucleic acid based binding molecules include aptamers. As used herein, the term "aptamer" means a single-stranded, partially single-stranded, partially double-stranded or double-stranded nucleotide sequence capable of specifically recognizing a selected non-oligonucleotide molecule or group of molecules by a mechanism other than Watson-Crick base pairing or triplex formation. Aptamers can include, without limitation, defined sequence segments and sequences comprising nucleotides, ribonucleotides, deoxyribonucleotides, nucleotide analogs, modified nucleotides and nucleotides comprising backbone modifications, branchpoints and nonnucleotide residues, groups or bridges. Methods for selecting aptamers for binding to a molecule are widely known in the art and easily accessible to one of ordinary skill in the art.

In some embodiments of the aspects described herein, the binding molecules are polyclonal and/or monoclonal antibodies and antigen-binding derivatives or fragments thereof. Well-known antigen binding fragments include, for example, single domain antibodies (dAbs; which consist essentially of single VL or VH antibody domains), Fv fragment, including single chain Fv fragment (scFv), Fab fragment, and F(ab')2 fragment. Methods for the construction of such antibody molecules are well known in the art. Accordingly, as used herein, the term "antibody" refers to an intact immunoglobulin or to a monoclonal or polyclonal antigen-binding fragment with the Fc (crystallizable fragment) region or FcRn binding fragment of the Fc region. Antigen-binding fragments may be produced by recombinant DNA techniques or by enzymatic or chemical cleavage of intact antibodies. "Antigen-binding fragments" include, inter alia, Fab, Fab', F(ab')2, Fv, dAb, and complementarity determining region (CDR) fragments, single-chain antibodies (scFv), single domain antibodies, chimeric antibodies, diabodies and polypeptides that contain at least a portion of an immunoglobulin that is sufficient to confer specific antigen binding to the polypeptide. The terms Fab, Fc, pFc', F(ab') 2 and Fv are employed with standard immunological meanings (Klein, Immunology (John Wiley, New York, N.Y., 1982); Clark, W. R. (1986) The Experimental Foundations of Modern Immunology (Wiley & Sons, Inc., New York); and Roitt, I. (1991) Essential Immunology, 7th Ed., (Blackwell Scientific Publications, Oxford)). Antibodies or antigen-binding fragments specific for various antigens are available commercially from vendors such as R&D Systems, BD Biosciences, e-Biosciences and Miltenyi, or can be raised against these cell-surface markers by methods known to those skilled in the art.

In some embodiments, the binding molecule binds with a cell. Without wishing to be bound by theory, a molecule that binds with a cell can do so by binding with a cell-surface marker or a cell-surface molecule. These binding molecules that bind with a cell are also referred to as cell binding molecules. In some further embodiments, the binding molecule binds with a cell-surface marker but does not cause initiation of downstream signaling event mediated by that cell-surface marker. Binding molecules specific for cell-surface molecules include, but are not limited to, antibodies or fragments thereof, natural or recombinant ligands, small molecules, nucleic acids and analogues thereof, intrabodies, aptamers, lectins, and other proteins or peptides.

As used herein, a "cell-surface marker" refers to any molecule that is present on the outer surface of a cell. Some molecules that are normally not found on the cell-surface can be engineered by recombinant techniques to be expressed on the surface of a cell. Many naturally occurring cell-surface markers present on mammalian cells are termed "CD" or "cluster of differentiation" molecules. Cell-surface markers often provide antigenic determinants to which antibodies can bind to.

Accordingly, as defined herein, a "binding molecule specific for a cell-surface marker" refers to any molecule that can selectively react with or bind to that cell-surface marker, but has little or no detectable reactivity to another cell-surface marker or antigen. Without wishing to be bound by theory, affinity molecules specific for cell-surface markers generally recognize unique structural features of the markers. In some embodiments of the aspects described herein, the affinity molecules specific for cell-surface markers are polyclonal and/or monoclonal antibodies and antigen-binding derivatives or fragments thereof.

In some embodiments, the cell binding molecule is a ligand that binds to a receptor on the surface of a cell. Such a ligand can be a naturally occurring molecule, a fragment thereof or a synthetic molecule or fragment thereof. In some embodiments, the ligand is non-natural molecule selected for binding with a target cell. High throughput methods for selecting non-natural cell binding ligands are known in the art and easily available to one of skill in the art. See for example, Anderson, et al., Biomaterial microarrays: rapid, microscale screening of polymer-cell interaction. *Biomaterials* (2005) 26:4892-4897; Anderson, et al., Nanoliter-scale synthesis of arrayed biomaterials and application to human embryonic stem cells. *Nature Biotechnology* (2004) 22:863-866; Orner, et al., Arrays for the combinatorial exploration of cell adhesion. *Journal of the American Chemical Society* (2004) 126:10808-10809; Falsey, et al., Peptide and small molecule microarray for high throughput cell adhesion and functional assays. *Bioconjugate Chemistry* (2001) 12:346-353; Liu, et al., *Biomacromolecules* (2001) 2(2): 362-368; and Taurniare, et al., *Chem. Comm.* (2006): 2118-2120.

In some embodiments, the cell binding molecule is an integrin-binding peptide. In some embodiments, the integrin-binding peptide comprises the amino acid sequence Arg-Gly-Asp (RGD). In some embodiments, the cell binding molecule is a peptide comprising the amino acid sequence $(Gly)_4$-Arg-Gly-Asp-Ala-Ser-Ser-Lys-Tyr (SEQ ID NO: 1).

The cryogel comprising the bioactive agent can be delivered to an in vivo locus. Exemplary in vivo loci include, but are not limited to site of a wound, trauma or disease. The composition can be delivered to the in vivo locus by, for example, implanting the compositions into a subject.

Compositions that are to be implanted can additionally include one or more additives. Additives can be resolving (biodegradable) polymers, mannitol, starch sugar, inosite, sorbitol, glucose, lactose, saccharose, sodium chloride, calcium chloride, amino acids, magnesium chloride, citric acid, acetic acid, hydroxyl-butanedioic acid, phosphoric acid, glucuronic acid, gluconic acid, poly-sorbitol, sodium acetate, sodium citrate, sodium phosphate, zinc stearate, aluminium stearate, magnesium stearate, sodium carbonate, sodium bicarbonate, sodium hydroxide, polyvinylpyrolidones, polyethylene glycols, carboxymethyl celluloses, methyl celluloses, starch or their mixtures.

The implant can have virtually any regular or irregular shape including, but not limited to, spheroid, cubic, polyhedron, prism, cylinder, rod, disc, or other geometric shape.

Accordingly, in some embodiments, the implant is of cylindrical form from about 0.5 to about 10 mm in diameter and from about 0.5 to about 10 cm in length. Preferably, its diameter is from about 1 to about 5 mm and length from about 1 to about 5 cm.

In some embodiments, the implant is of spherical form. When the implant is in a spherical form, its diameter can range from about 0.5 to about 50 mm in diameter. In some embodiments, a spherical implant's diameter is from about 5 to about 30 mm. Preferably the diameter is from about 10 to about 25 mm.

In some embodiments, the cryogel comprises a detectable molecule, e.g., a dye. As used herein, the term "detectable molecule" refers to an element or functional group in a molecule that allows for the detection, imaging, and/or monitoring of the presence of the molecule. The detectable molecule can be an echogenic substance (either liquid or gas), non-metallic isotope, an optical reporter, a boron neutron absorber, a paramagnetic metal ion, a ferromagnetic metal, a gamma-emitting radioisotope, a positron-emitting radioisotope, or an x-ray absorber.

Suitable optical reporters include, but are not limited to, fluorescent reporters and chemiluminescent groups. A wide variety of fluorescent reporter dyes are known in the art. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluorescein, rhodamine or other like compound. Suitable fluorescent reporters include xanthene dyes, such as fluorescein or rhodamine dyes, including, but not limited to, Alexa Fluor® dyes (InvitrogenCorp.; Carlsbad, Calif.), fluorescein, fluorescein isothiocyanate (FITC), Oregon Green™, rhodamine, Texas red, tetrarhodamine isothiocynate (TRITC), 5-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N,N'-tetramefhyl-6-carboxyrhodamine (TAMRA), 6-carboxy-X-rhodamine (ROX). Suitable fluorescent reporters also include the naphthylamine dyes that have an amino group in the alpha or beta position. For example, naphthylamino compounds include 1-dimethylamino-naphthyl-5-sulfonate, 1-anilino-8-naphthalene sulfonate, 2-p-toluidinyl-6-naphthalene sulfonate, and 5-(2'-aminoethyl)aminonaphthalene-1-sulfonic acid (EDANS). Other fluorescent reporter dyes include coumarins, such as 3-phenyl-7-isocyanatocoumarin; acridines, such as 9-isothiocyanatoacridine and acridine orange; N-(p(2-benzoxazolyl)phenyl)maleimide; cyanines, such as Cy2, indodicarbocyanine 3 (Cy3), indodicarbocyanine 5 (Cy5), indodicarbocyanine 5.5 (Cy5.5), 3-(-carboxy-pentyl)-3'ethyl-5,5'-dimethyloxacarbocyanine (CyA); 1H,5H,11H,15H-Xantheno[2,3,4-ij:5,6,7-i'j']diquinolizin-18-ium, 9-[2 (or 4)-[[[6-[2,5-dioxo-1-pyrrolidinyl)oxy]-6-oxohexyl]amino]sulfonyl]-4(or 2)-sulfophenyl]-2,3,6,7,12,13,16,17octahydro-inner salt (TR or Texas Red); BODIPY™ dyes; benzoxadiazoles; stilbenes; pyrenes; and the like. Many suitable forms of these fluorescent compounds are available and can be used.

Examples of fluorescent proteins suitable for use as imaging agents include, but are not limited to, green fluorescent protein, red fluorescent protein (e.g., DsRed), yellow fluorescent protein, cyan fluorescent protein, blue fluorescent protein, and variants thereof (see, e.g., U.S. Pat. Nos. 6,403,374, 6,800,733, and 7,157,566). Specific examples of GFP variants include, but are not limited to, enhanced GFP (EGFP), destabilized EGFP, the GFP variants described in Doan et al, *Mol. Microbiol,* 55:1767-1781 (2005), the GFP variant described in Crameri et al, *Nat. Biotechnol.,* 14:315319 (1996), the cerulean fluorescent proteins described in Rizzo et al, *Nat. Biotechnol,* 22:445 (2004) and Tsien, *Annu. Rev. Biochem.,* 67:509 (1998), and the yellow fluorescent protein described in Nagal et al, *Nat. Biotechnol.,* 20:87-90 (2002). DsRed variants are described in, e.g., Shaner et al, *Nat. Biotechnol.,* 22:1567-1572 (2004), and include mStrawberry, mCherry, mOrange, mBanana, mHoneydew, and mTangerine. Additional DsRed variants are described in, e.g., Wang et al, *Proc. Natl. Acad. Sci. U.S.A.,* 101:16745-16749 (2004) and include mRaspberry and mPlum. Further examples of DsRed variants include mRFPmars described in Fischer et al, *FEBS Lett.,* 577:227-232 (2004) and mRFPruby described in Fischer et al, *FEBS Lett,* 580:2495-2502 (2006).

Suitable echogenic gases include, but are not limited to, a sulfur hexafluoride or perfluorocarbon gas, such as perfluoromethane, perfluoroethane, perfluoropropane, perfluorobutane, perfluorocyclobutane, perfluropentane, or perfluorohexane.

Suitable non-metallic isotopes include, but are not limited to, $^{11}C$, $^{14}C$, $^{13}N$, $^{18}F$, $^{123}I$, $^{124}I$, and $^{125}I$. Suitable radioisotopes include, but are not limited to, $^{99}mTc$, $^{95}Tc$, $^{111}In$, $^{62}Cu$, $^{64}Cu$, Ga, $^{68}Ga$, and $^{153}Gd$. Suitable paramagnetic metal ions include, but are not limited to, Gd(III), Dy(III), Fe(III), and Mn(II). Suitable X-ray absorbers include, but are not limited to, Re, Sm, Ho, Lu, Pm, Y, Bi, Pd, Gd, La, Au, Au, Yb, Dy, Cu, Rh, Ag, and Ir. In some embodiments, the radionuclide is bound to a chelating agent or chelating agent-linker attached to the cryogel. Suitable radionuclides for direct conjugation include, without limitation, $^{18}F$, $^{124}I$, $^{125}I$, $^{131}I$, and mixtures thereof. Suitable radionuclides for use with a chelating agent include, without limitation, $^{47}Sc$, $^{64}Cu$, $^{67}Cu$, $^{89}Sr$, $^{86}Y$, $^{87}Y$, $^{90}Y$, $^{105}Rh$, $^{111}Ag$, $^{111}In$, $^{117}mSn$, $^{149}Pm$, $^{153}Sm$, $^{166}Ho$, $^{177}Lu$, $^{186}Re$, $^{188}Re$, $^{211}At$, and mixtures thereof. Suitable chelating agents include, but are not limited to, DOTA, BAD, TETA, DTPA, EDTA, NTA, HDTA, their phosphonate analogs, and mixtures thereof.

A detectable response generally refers to a change in, or occurrence of, a signal that is detectable either by observation or instrumentally. In certain instances, the detectable response is fluorescence or a change in fluorescence, e.g., a change in fluorescence intensity, fluorescence excitation or emission wavelength distribution, fluorescence lifetime, and/or fluorescence polarization. One of skill in the art will appreciate that the degree and/or location of labeling in a subject or sample can be compared to a standard or control (e.g., healthy tissue or organ). In certain other instances, the detectable response the detectable response is radioactivity (i.e., radiation), including alpha particles, beta particles, nucleons, electrons, positrons, neutrinos, and gamma rays emitted by a radioactive substance such as a radionuclide.

In another aspect, the invention provides an on-demand method for controlling the release of a bioactive agent (e.g. a drug), the method comprising: (a) providing or administering to a subject a cryogel described herein, wherein the cryogel comprises the bioactive agent; and (b) inducing a change in porosity, pore size, pore connectivity, swelling agent concentration, and/or specific volume of the composition via an electrical stimulus to control the release of the bioactive agent. As used herein, the term "on-demand" refers to the operator control over the release of bioactive agent from the cryogel.

Release of the bioactive agent can be achieved in a pulsatile manner by repeated application of external stimulus. This ability for on-demand pulsatile release of bioactive agents is useful in a variety of settings, including immunizations, which typically provide an initial immunization, followed by distinct booster doses at later times. Moreover, repeated administration of well-defined doses of allergen, in the absence of immunostimulatory molecules, from such a polymer matrix may be useful for inducing tolerance. It also can be advantageous to use an external stimulus to deliver bioactive agents in a pulsatile manner so as to time the delivery to coincide with a particular biological event (e.g. the circadian rhythm) in order to maximize the effectiveness of the bioactive agent (e.g. against tumors).

In some cases, the cryogel can release the bioactive agent continuously, and application of stimulus allows release to of the bioactive agent to be decreased or stopped in emergent clinical situations. For example, an implantable cryogel can be designed to hold a chemotherapeutic therapeutic agent. In the presence of a primary electrical stimulus, the therapeutic agent will continuously disperse out from the composition, however, in the presence of a second electrical field rate of dispersion will be lowered. This can be useful, for example, when there is a need to hold chemotherapeutic therapeutic agents with immunodepressant side-effects while treating infections.

In another example, an implantable cryogel can be designed to hold an agent such that there is little or no release of the agent in the absence of stimulus. Without the presence of applied electrical stimulus, little or no agent will disperse out from the cryogel, however, in the presence of an applied magnetic field rate of dispersion will be increased. This can be useful, for example, when there is a need to hold release of an agent from the cryogel after placement in a subject. The agent could then be released at a required and/or suitable time by applying the electrical stimulus.

The cryogel comprising the bioactive agent can be delivered to an in vivo locus in a subject. Exemplary in vivo loci include, but are not limited to site of a wound, trauma or disease. The cryogel can be delivered to the in vivo locus by, for example, implanting the compositions into a subject. Cryogels that are to be implanted can additionally include one or more additives. Additives can be resolving (biodegradable) polymers, mannitol, starch sugar, inosite, sorbitol, glucose, lactose, saccharose, sodium chloride, calcium chloride, amino acids, magnesium chloride, citric acid, acetic acid, hydroxyl-butanedioic acid, phosphoric acid, glucuronic acid, gluconic acid, poly-sorbitol, sodium acetate, sodium citrate, sodium phosphate, zinc stearate, aluminium stearate, magnesium stearate, sodium carbonate, sodium bicarbonate, sodium hydroxide, polyvinylpyrolidones, polyethylene glycols, carboxymethyl celluloses, methyl celluloses, starch or their mixtures.

The implant can have virtually any regular or irregular shape including, but not limited to, spheroid, cubic, polyhedron, prism, cylinder, rod, disc, or other geometric shape. Accordingly, in some embodiments, the implant is of cylindrical form from about 0.5 to about 10 mm in diameter and from about 0.5 to about 10 cm in length. Preferably, its diameter is from about 1 to about 5 mm and length from about 1 to about 5 cm.

In some embodiments, the implant is of spherical form. When the implant is in a spherical form, its diameter can range from about 0.5 to about 50 mm in diameter. In some embodiments, a spherical implant's diameter is from about 5 to about 30 mm. Preferably the diameter is from about 10 to about 25 mm.

Due to its large deformation, fast response, reversible motion and biocompatibility, the electro-responsive cryogel described herein can be used in a physiological environment as a bioactuator. For example, it can be used as a electrically controlled artificial muscle.

A significant amount of solvent flows into/out of the cryogel during its deformation. Therefore, one can use electrical stimulus to drive the cryogel to act as a pump in microfluidic chips. Further, the reversible deformation of the cryogel can also be used as valves in microfluidic chips to open or close microfluidic channels.

Deformation sensitive pigments can also be added into the cryogel (Lu Y. F. et al., Nature (2001) 410:19). Electrical stimulus induces the deformation of the gel, as well as the pigments encapsulated in it. Therefore, the pigments can change color or florescence in response to electrical stimulus.

Owing to fast response times and substantial specific volume changes in response to an external stimulus, compositions described herein can be employed for numerous applications, particularly in medicine, pharmaceutics, drug-delivery, biosensors, bio-actuators, optical devices, valves and pumps for microfluidics, separation and membranes, purifications, and enzyme and cell immobilization. See for example, Qiu, Y. and Park, K. Adv Drug Delivery Rev (2001), 53: 321-339; Miyata, T. Urgami, T. and Nakamae, K. Adv. Drug Delivery Rev. (2002), 54: 79-98; Bckiari, V. et al., Langmuir (2004), 20: 7972; Lopes, D. Cendoya, L. and Mijangos, C. Macromol Symp (2001), 166:173; Lao, L. and Ramanujan, V. R. J Mater Sci Mater Med (2004), 15: 1061; Porter, J. and Pickup, R. W. J. Microbiol Methods (1998), 33: 221; Xie, X. et al., J Magn Mater (2004), 227: 16 and Gupta, P. K. and Hung, C. T. Life Sci (19889) 44, 175.

For administration to a subject, the cryogel can be provided in pharmaceutically acceptable (e.g., sterile) compositions. Accordingly, another aspect described herein is a pharmaceutical composition comprising a cryogel and a pharmaceutically acceptable carrier. These pharmaceutically acceptable compositions comprise a cryogel formulated together with one or more pharmaceutically acceptable carriers (additives) and/or diluents. As described in detail below, the pharmaceutical compositions of the present disclosure can be specifically formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and/or systemic absorption), boluses, powders, granules, pastes for application to the tongue; (2) parenteral administration, for example, by subcutaneous, intramuscular, intravenous (e.g., bolus or infusion) or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960, content of all of which is herein incorporated by reference.

As used herein, the term "pharmaceutically acceptable" or "pharmacologically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Moreover, for animal (e.g., human) administration, it will be understood that compositions should meet sterility, pyrogenicity, general safety and purity standards as required by FDA Office of Biological Standards.

As used herein, the term "pharmaceutically acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alchols, such as ethanol; and (23) other non-toxic compatible substances employed in pharmaceutical formulations. Wetting agents, coloring agents, release agents, coating agents, disintegrating agents, binders, sweetening agents, flavoring agents, perfuming agents, protease inhibitors, plasticizers, emulsifiers, stabilizing agents, viscosity increasing agents, film forming agents, solubilizing agents, surfactants, preservative and antioxidants can also be present in the formulation. The terms such as "excipient", "carrier", "pharmaceutically acceptable carrier" or the like are used interchangeably herein.

Embodiments of the invention can be described by one or more of the following numbered paragraphs:

1. An electro-responsive cryogel, wherein the cryogel comprises a matrix comprising interconnected macropores therein and the matrix comprises cross-linked charged monomers.
2. The electro-responsive cryogel of paragraph 1, wherein the cryogel comprises pores having mean pore diameter in range of about 0.01 μm to 1000 μm.

3. The electro-responsive cryogel of any of paragraphs 1-2, wherein the cryogel has porosity of 0.1 to 0.99.
4. The electro-responsive cryogel of any of paragraphs 1-3, wherein the cryogel has an elastic modulus of less than 10 kPa.
5. The electro-responsive cryogel of any of paragraphs 1-4, wherein the cryogel undergoes a change in its porosity, pore size, pore connectivity, swelling agent concentration, and/or specific volume in response to an electrical stimulus.
6. The electro-responsive cryogel of any of paragraphs 1-6, wherein the cryogel undergoes a change in its porosity, pore size, pore connectivity, swelling agent concentration, and/or specific volume in response to an electrical stimulus by at least 5% within 1 hour of application of the electrical stimulus.
7. The electro-responsive cryogel of paragraph 6 or 7, wherein the electrical stimulus is from 1V to 500V.
8. The electro-responsive cryogel of any of paragraphs 1-7, wherein the cryogel undergoes a change in its porosity, pore size, pore connectivity, swelling agent concentration, and/or specific volume in response to an electrical stimulus and reverts to within 15% of its original value when the stimulus is discontinued.
9. The electro-responsive cryogel of any of paragraphs 1-8, wherein the charged monomers are selected from the group consisting of acrylic acid (AAc), methacrylic acid, 3-(acrylamido)phenylboronic acid, and derivatives and any combinations thereof
10. The electro-responsive cryogel of any of paragraphs 1-9, wherein the charged monomers are cross-linked by a cross-linker selected from the group consisting of N,N'-methylenebis-acrylamide (BA), polyethyleneglycol di(meth)acrylate (PEG-DM), and any combination thereof
11. The electro-responsive cryogel of any of paragraphs 1-10, wherein the charged monomers are 0.01% to 99% by weight of the cryogel.
12. The electro-responsive cryogel of any of paragraphs 1-11, wherein the cross-linker are from 0.01% to 10% by weight of the cryogel.
13. The electro-responsive cryogel of any of paragraphs 1-12, wherein the charged monomers and the cross-linker are in ratio from 100:1 to 1:1 by weight, volume or mol.
14. The electro-responsive cryogel of any of paragraphs 1-13, wherein the matrix further comprises uncharged monomers cross-linked with the charged monomers.
15. The electro-responsive cryogel of paragraph 15, wherein the uncharged monomers are selected from the group consisting of N-substituted and non-substituted acrylamides; N-substituted and non-substituted (meth)acrylamides; N-alkyl substituted N-vinylamides; Hydroxyalkyl (meth)acrylates; vinylacetate; alkylethers of vinyl alcohols; styrene and ring substituted styrene derivatives; vinyl monomers; and any combinations thereof;
16. The electro-responsive cryogel of paragraph 14 or 15, wherein the uncharged monomers are selected from the group consisting of acrylamide (AAm), methacrylamide, N,N-diallyl acrylamide, diallyltartaramide, N-butyracrylamide, N-(2-hydroxypropyl)methacrylamide, N,N-dimethylaminoethylmethacrylate, N-isopropylacrylamide, glycidylmethacrylate, hydroxyethyl methacrylate, N,N'-methylenebis-acrylamide, N,N'-methylene-bis-methacrylamide, N,N'-hexamethylene-bis-acrylamide, N,N-diethylacrylamide, N-isopropylacrylamide, (2-(methacryloyloxy)ethyl)-trimethyl ammonium chloride, N-vinyl imidazole, diallylacryalamide, polyethyleneglycol di(meth)acrylate, polypropylene glycol diglycidyl ether, 3-(acrylamido)phenylboronic acid, and derivatives and any combinations thereof.
17. The electro-responsive cryogel of any of paragraphs 14-16, wherein the uncharged monomers are 0.01% to 99% by weight of the cryogel.
18. The electro-responsive cryogel of any of paragraphs 14-17, wherein the ratio of charged monomers to uncharged monomers is from about 100:1 to about 1:100 by weight, volume or mol.
19. The electro-responsive cryogel of any of paragraphs 1-18, wherein the cryogel further comprises a molecule selected from the group consisting of small organic or inorganic molecules; saccharines; monosaccharides; disaccharides; trisaccharides; oligosaccharides; polysaccharides; peptides; proteins, peptide analogs and derivatives; peptidomimetics; antibodies (polyclonal and monoclonal); antigen binding fragments of antibodies; nucleic acids; nucleic acid analogs and derivatives; an extract made from biological materials; naturally occurring or synthetic compositions; and any combinations thereof; and any combinations thereof.
20. The electro-responsive cryogel of paragraph 19, wherein the molecule is a therapeutic agent, a biological cell, or a detectable molecule.
21. A macroporous electro-responsive cryogel, wherein the cryogel is prepared by: polymerizing an aqueous solution of charged monomers and cross-linker monomers under freezing at a temperature below the freezing temperature of aqueous solvent.
22. The macroporous electro-responsive cryogel of paragraph 21, wherein the charged monomers are selected from the group consisting of acrylic acid (AAc), methacrylic acid, 3-(acrylamido)phenylboronic acid, and derivatives and any combinations thereof.
23. The macroporous electro-responsive cryogel of any of paragraphs 21-22, wherein the cross-linker is selected from the group consisting of N,N'-methylenebis-acrylamide (BA), polyethyleneglycol di(meth)acrylate (PEG-DM), and any combination thereof
24. The macroporous electro-responsive cryogel of any of paragraphs 21-23, wherein the charged monomer are acrylic acid and the cross-linker monomer are N,N'-methylenebis-polyethyleneglycol di(meth)acrylate.
25. The macroporous electro-responsive cryogel of any of paragraphs 21-24, wherein the charged monomers are 0.01% to 50% by weight, volume or mol of the aqueous solution.
26. The macroporous electro-responsive cryogel of any of paragraphs 21-25, wherein the cross-linker are from 0.01% to 10% by weight, volume or mol of aqueous solution.
27. The macroporous electro-responsive cryogel of any of paragraphs 21-26, wherein the charged monomers and the cross-linker are in ratio from 100:1 to 1:1 by weight, volume or mol.
28. The macroporous electro-responsive cryogel of any of paragraphs 21-27, wherein the aqueous solution further comprises uncharged monomers.
29. The macroporous electro-responsive cryogel of paragraph 28, wherein the uncharged monomers are selected from the group consisting of N-substituted and non-substituted acrylamides; N-substituted and non-substituted (meth)acrylamides; N-alkyl substituted N-vinylamides; Hydroxyalkyl (meth)acrylates; vinylacetate; alkylethers of vinyl alcohols; styrene and ring substituted styrene derivatives; vinyl monomers; and any combinations thereof;

30. The macroporous electro-responsive cryogel of any of paragraphs 28-29, wherein the uncharged monomers are selected from the group consisting of acrylamide (AAm), methacrylamide, N,N-diallyl acrylamide, diallyltartaramide, N-butyracrylamide, N-(2-hydroxypropyl)methacrylamide, N,N-dimethylaminoethylmethacrylate, N-isopropylacrylamide, glycidylmethacrylate, hydroxyethyl methacrylate, N,N'-methylenebis-acrylamide, N,N'-methylene-bis-methacrylamide, N,N'-hexamethylene-bis-acrylamide, N,N-diethylacrylamide, N-isopropylacrylamide, (2-(methacryloyloxy)ethyl)-trimethyl ammonium chloride, N-vinyl imidazole, diallylacryalamide, polyethyleneglycol di(meth)acrylate, polypropylene glycol diglycidyl ether, 3-(acrylamido) phenylboronic acid, and derivatives and any combinations thereof.

31. The macroporous electro-responsive cryogel of any of paragraphs 28-30, wherein the charged monomer are acrylic acid, uncharged monomers are acrylamide, and the cross-linker monomer are N,N'-methylenebis-acrylamide or polyethyleneglycol di(meth)acrylate.

32. The macroporous electro-responsive cryogel of any of paragraphs 28-31, wherein the uncharged monomers are 0.01% to 50% by weight, volume or mol of the aqueous solution.

33. The macroporous electro-responsive cryogel of any of paragraphs 28-32, wherein the ratio of charged monomers to uncharged monomers is from about 100:1 to about 1:100 by weight, volume or mol.

34. The macroporous electro-responsive cryogel of any of paragraphs 21-33, wherein the charged monomer, the uncharged monomer, and the cross-linker monomer are in a ratio 4:4:0.1 by weight, volume or mol.

35. The macroporous electro-responsive cryogel of any of paragraphs 21-34, wherein the solvent is selected from the group consisting of water and mixtures of water and water-miscible organic solvents.

36. The macroporous electro-responsive cryogel of any of paragraphs 21-35, wherein the cryogel further comprises a compound selected from the group consisting of small organic or inorganic molecules; saccharines; monosaccharides; disaccharides; trisaccharides; oligosaccharides; polysaccharides; peptides; proteins, peptide analogs and derivatives; peptidomimetics; antibodies (polyclonal and monoclonal); antigen binding fragments of antibodies; nucleic acids; nucleic acid analogs and derivatives; an extract made from biological materials; naturally occurring or synthetic compositions; and any combinations thereof; and any combinations thereof.

37. The macroporous electro-responsive cryogel of any of paragraphs 36, wherein the molecule is a therapeutic agent, a biological cell, or a detectable molecule.

38. The macroporous electro-responsive cryogel of any of paragraphs 21-37, wherein the polymerization carried out at a temperature at least 5° C. below the freezing temperature of the solvent.

39. The macroporous electro-responsive cryogel of any of paragraphs 21-38, wherein the polymerization carried out at a temperature from −5° C. to −40° C.

40. The macroporous electro-responsive cryogel of any of paragraphs 21-39, wherein the cryogel comprises pores having mean pore diameter in range of about 0.01 μm to 1000 μm.

41. The macroporous electro-responsive cryogel of any of paragraphs 21-40, wherein the cryogel has porosity of 0.1 to 0.99.

42. A method for preparation of an electro-responsive cryogel, the method comprising: polymerizing an aqueous solution of charged monomers and cross-linker monomers under freezing at temperature below the freezing temperature of aqueous solvent.

43. A method for controlling the release of a bioactive agent, the method comprising: (a) providing a macroporus electro-responsive cryogel of any paragraphs 21-41, wherein the cryogel comprises the bioactive agent; and (b) inducing a change in porosity, pore size, pore connectivity, swelling agent concentration, and/or specific volume of the composition via an electrical stimulus to control the release of the bioactive agent.

44. A method for controlling the release of a bioactive agent, the method comprising: (a) providing an electro-responsive cryogel of any paragraphs 1-20, wherein the cryogel comprises the bioactive agent; and (b) inducing a change in porosity, pore size, pore connectivity, swelling agent concentration, and/or specific volume of the composition via an electrical stimulus to control the release of the bioactive agent.

Some Selected Definitions

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

As used herein the term "comprising" or "comprises" is used in reference to compositions, methods, and respective component(s) thereof, that are essential to the invention, yet open to the inclusion of unspecified elements, whether essential or not.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean±5% of the value being referred to. For example, about 100 means from 95 to 105.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. The terms, "patient" and "subject" are used interchangeably herein. A subject can be male or female.

Preferably, the subject is a mammal. The mammal can be a human, non-human primate, mouse, rat, dog, cat, horse, or cow, but are not limited to these examples. Mammals other than humans can be advantageously used as subjects that represent animal models of human diseases and disorders. In addition, compounds, compositions and methods described herein can be used to treat domesticated animals and/or pets.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

As used herein, the term "administer" refers to the placement of a composition into a subject by a method or route which results in at least partial localization of the composition at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by intravenous infusion or injection.

Administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the compounds are formulated into ointments, salves, gels, or creams as generally known in the art.

In some embodiments, administration includes implanting a composition described herein in a subject.

The phrase "therapeutically-effective amount" as used herein means that amount of a compound, material, or composition comprising a compound described herein which is effective for producing some desired therapeutic effect in at least a sub-population of cells in a subject at a reasonable benefit/risk ratio applicable to any medical treatment. Thus, "therapeutically effective amount" means that amount which, when administered to a subject for treating a disease, is sufficient to effect such treatment for the disease.

Determination of an effective amount is well within the capability of those skilled in the art. Generally, the actual effective amount can vary with the specific compound, the use or application technique, the desired effect, the duration of the effect and side effects, the subject's history, age, condition, sex, as well as the severity and type of the medical condition in the subject, and administration of other pharmaceutically active agents. Accordingly, an effective dose of compound described herein is an amount sufficient to produce at least some desired therapeutic effect in a subject.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of use or administration utilized.

The effective dose can be estimated initially from cell culture assays. A dose can be formulated in animal models to achieve a circulating plasma concentration range that includes the $IC_{50}$ (i.e., the concentration of the therapeutic which achieves a half-maximal inhibition of symptoms) as determined in cell culture. Levels in plasma can be measured, for example, by high performance liquid chromatography. The effects of any particular dosage can be monitored by a suitable bioassay.

Generally, the term "treatment" or "treating" is defined as the application or administration of a therapeutic agent to a patient, or application or administration of a therapeutic agent to an isolated tissue or cell line from a patient, said patient having a disease, a symptom of disease or a predisposition toward a disease, with the purpose to cure, heal, alleviate, relieve, alter, remedy, ameliorate, improve or affect the disease, the symptoms of disease or the predisposition toward disease. Thus, treating can include suppressing, inhibiting, preventing, treating, or a combination thereof. Treating refers, inter alia, to increasing time to sustained progression, expediting remission, inducing remission, augmenting remission, speeding recovery, increasing efficacy of or decreasing resistance to alternative therapeutics, or a combination thereof "Suppressing" or "inhibiting", refers, inter alia, to delaying the onset of symptoms, preventing relapse to a disease, decreasing the number or frequency of relapse episodes, increasing latency between symptomatic episodes, reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof. In one embodiment the symptoms are primary, while in another embodiment symptoms are secondary. "Primary" refers to a symptom that is a direct result of a disorder, e.g., diabetes, while, secondary refers to a symptom that is derived from or consequent to a primary cause. Symptoms may be any manifestation of a disease or pathological condition.

Accordingly, as used herein, the term "treatment" or "treating" includes any administration of a compound described herein and includes: (i) preventing the disease from occurring in a subject which may be predisposed to the disease but does not yet experience or display the pathology or symptomatology of the disease; (ii) inhibiting the disease in an subject that is experiencing or displaying the pathology or symptomatology of the diseased (i.e., arresting further development of the pathology and/or symptomatology); or (iii) ameliorating the disease in a subject that is experiencing or displaying the pathology or symptomatology of the diseased (i.e., reversing the pathology and/or symptomatology).

By "treatment", "prevention" or "amelioration" of a disease or disorder is meant delaying or preventing the onset of such a disease or disorder, reversing, alleviating, ameliorating, inhibiting, slowing down or stopping the progression, aggravation or deterioration the progression or severity of a condition associated with such a disease or disorder. In one embodiment, the symptoms of a disease or disorder are alleviated by at least 5%, at least 10%, at least 20%, at least 30%, at least 40%, or at least 50%.

Efficacy of treatment is determined in association with any known method for diagnosing the disorder. Alleviation of one or more symptoms of the disorder indicates that the compound confers a clinical benefit. Any of the therapeutic methods described to above can be applied to any suitable subject including, for example, mammals such as dogs, cats, cows, horses, rabbits, monkeys, and most preferably, humans.

The term "derivative" as used herein refers to a chemical substance related structurally to another, i.e., an "original" substance, which can be referred to as a "parent" compound. A "derivative" can be made from the structurally-related parent compound in one or more steps. The phrase "closely related derivative" means a derivative whose molecular weight does not exceed the weight of the parent compound by more than 50%. The general physical and chemical properties of a closely related derivative are also similar to the parent compound.

The term "cryogel" refers to a gel that has been freeze dried. Analogously, a "polymer cryogel" is a polymer gel that has been freeze dried.

To the extent not already indicated, it will be understood by those of ordinary skill in the art that any one of the various embodiments herein described and illustrated can be further modified to incorporate features shown in any of the other embodiments disclosed herein.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

EXAMPLES

Example 1

Rapid and Extensive Collapse from Electrically Responsive Macroporous Hydrogels

Electrically responsive hydrogels hold potential utility in numerous areas including robotic actuation, microfluidic control, sensory technology, optical devices, drug delivery, and tissue engineering.[1-4] These polyelectrolytic[1,2] hydrogels are of particular interest in applications that demand the material properties of hydrogels coupled with precisely timed, stimuli-proportioned control.[3-4] Indeed, their compatibility with electrical circuitry and microprocessor-based control systems provides great potential in coordinating complex actuations while using simple and inexpensive equipment. Despite this promise, electrically responsive hydrogels have been plagued by poor responsivity, precluding their use in many applications. A previous investigation[5] describes the electro-collapsibility of such polyelectrolytic hydrogels as a two-part process where an electric field exerts (i) a force on the charged polymer which draws the gel towards one electrode and (ii) an opposite force that draws mobile counterions towards the opposing electrode and out of the gel. Therefore, rapid hydrogel responsivity requires a design that enhances the movement of both water and ions in and through the hydrogel. The time required for water and ion diffusion can be reduced by simply scaling down the size of the hydrogels,[6] but this does not directly address the need to facilitate transport. Larger electrically responsive hydrogels have been limited to response times of 30 minutes[7], to hours[8,9,10], or tens of hours[5].

Now, the inventors have discovered that the addition of interconnected macropores unexpectedly, surprisingly can enhance a polyelectrolytic hydrogel's ability to collapse when subjected to electrical stimulation. Without wishing to be bound by a theory, an interconnected pore structure allows for more efficient syneresis of water and egression of ions from the hydrogel, thus providing greater responsivity. Additionally, apparent reductions in gel volume can be directly related to the volumetric collapse of macropores and not large-scale polymer rearrangement and/or polymer translocation per se. This can allow for more rapid reductions in gel volume while preserving the structural integrity of the gel. Finally, an interconnected macroporous structure would render the gel much softer, and therefore more electromechanically mutable.

Figure 1C:
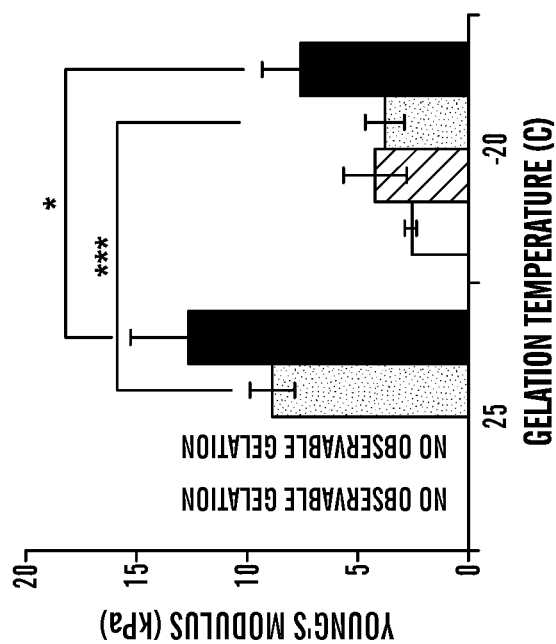
Figure 1B:
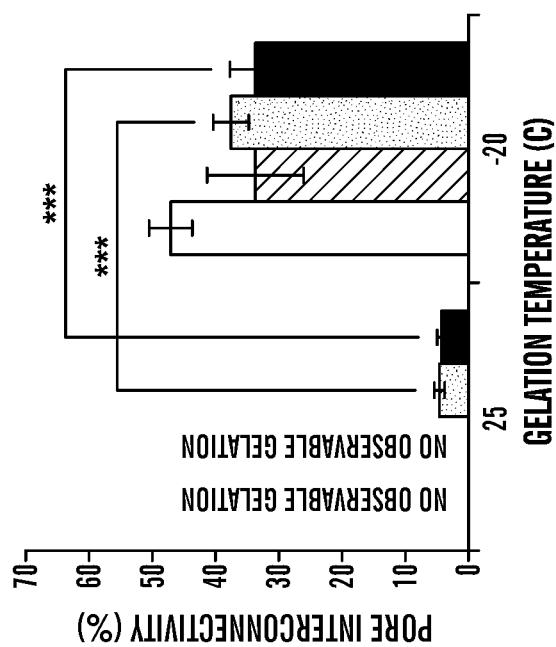
Figure 1E:
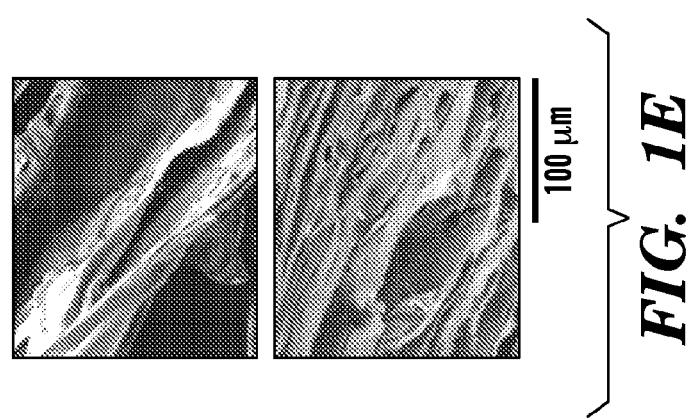
Figure 1D:
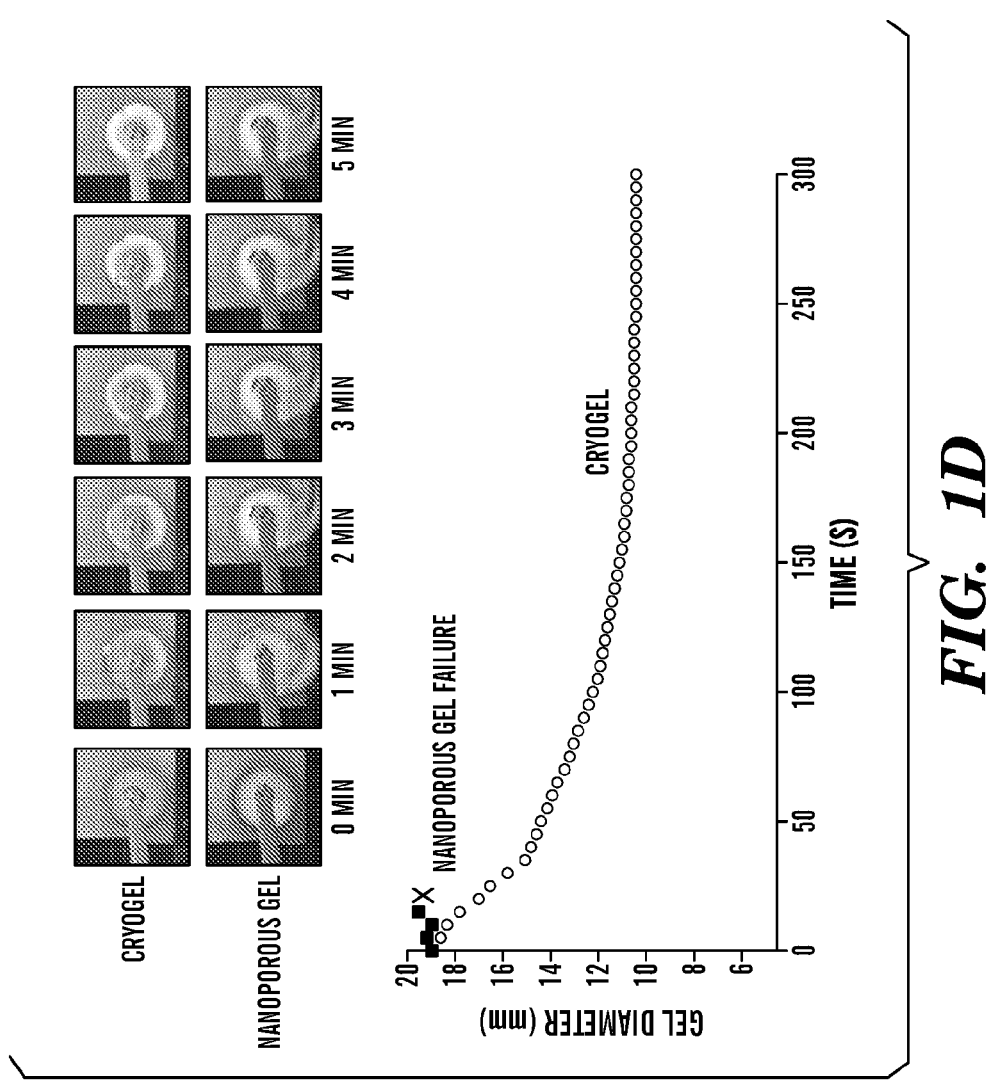
Figure 5A:
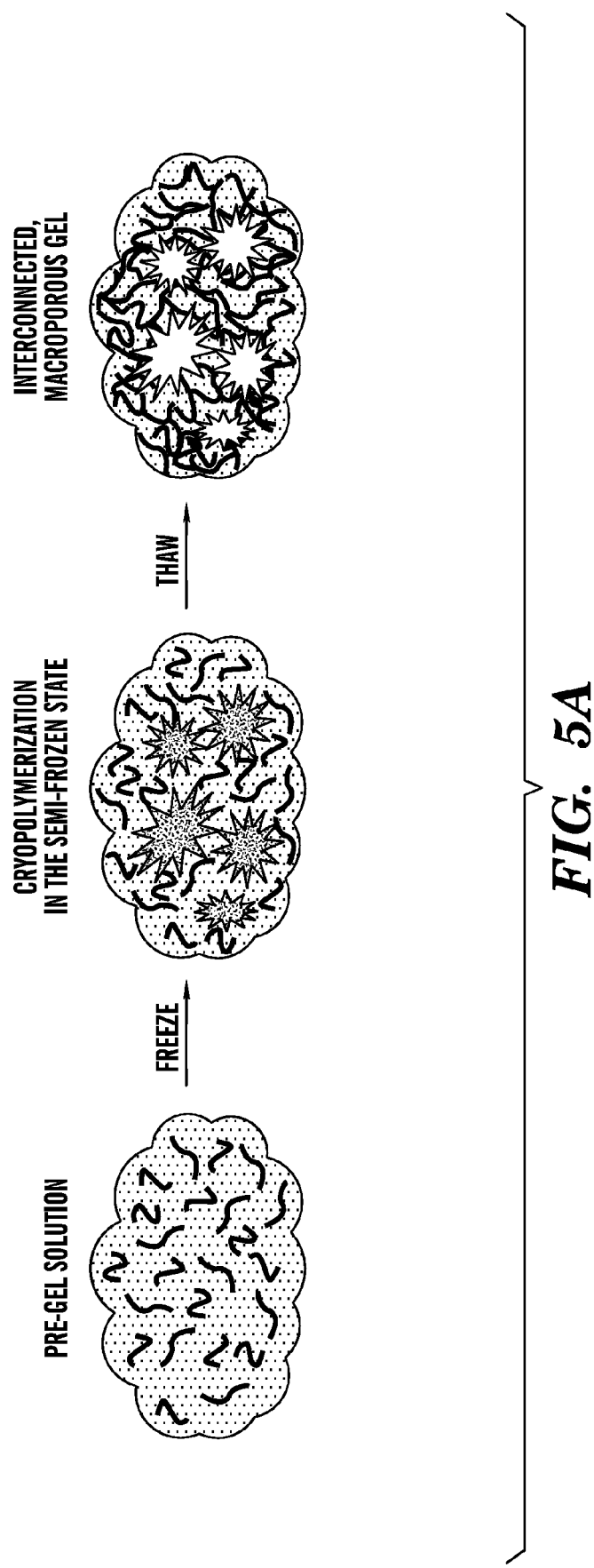
FIGS. 5A-5C shows that the polyanionic, macroporous gels used in this study were made with a cryopolymerization approach and can be monitored in an experimental apparatus capable of collapsing polyanionic gels inward by generating an outward, radial electric field.

The inventors used a cryopolymerization approach[11,12] (FIG. 5) to fabricate macroporous electrogels. Essentially, gels were formed in a semi-frozen state, as nascent ice crystals concentrate monomer into the space between them in this process, thus forming a concentrated gel structure interstitially between ice crystals following polymerization. When gels were thawed, ice crystals melted, leaving voids or pores. Cryogels fabricated from acrylic acid (AAc) and acrylamide (AAm) exhibited large, interconnected pores while gels formed at room temperature had no large pores (FIG. 1A). The composition of the polymeric network influenced the macropore morphology. As total polymeric content increased, pores were generally more aligned and planar, but at the highest polymer concentrations the walls between pores became thicker. Quantification of gel properties confirmed that cryogels exhibited much higher degrees of pore interconnectivity (FIG. 1B) and lower modulus (FIG. 1C) than their room-temperature-polymerized, nanoporous counterparts. Note that at low overall polymer content, only cryogels were successfully formed. This is likely due to the increase in polymer concentration between ice crystals during cryotreatment. Macroporous cryogels were able to rapidly collapse to small diameters without loss of structural integrity when exposed to 50 V in deionized water, while nanoporous gels of the same makeup fragmented after about 30 seconds (FIG. 1D). The ability to undergo large and rapid volumetric changes was associated with the transition of the cryogels' macropores from an open (FIG. 1E, top) to a closed state (FIG. 1E, bottom). The rapid and extensive collapse observed here was primarily due to exposure to an electric field (estimated to be a radially graded field between 20-80 V cm$^{-1}$), with electrochemically induced changes in pH and ionic content having secondary roles (Supporting Information, Fig. S2 FIG. 6).

Figure 2A:
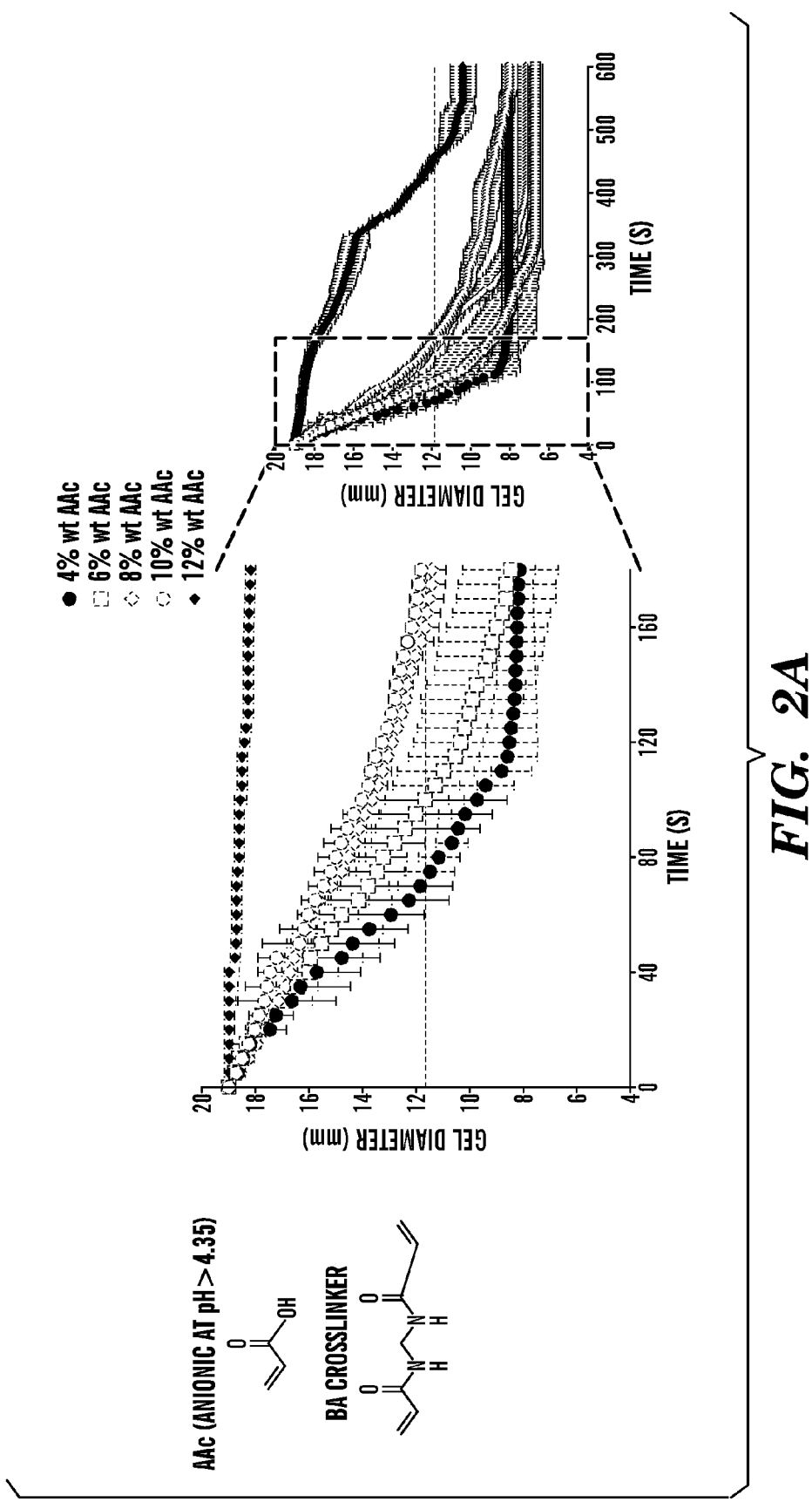
FIGS. 2A-2D show the rate and extent of electrical collapse depends on the hydrogel polymer type and amount.
Figure 2C:
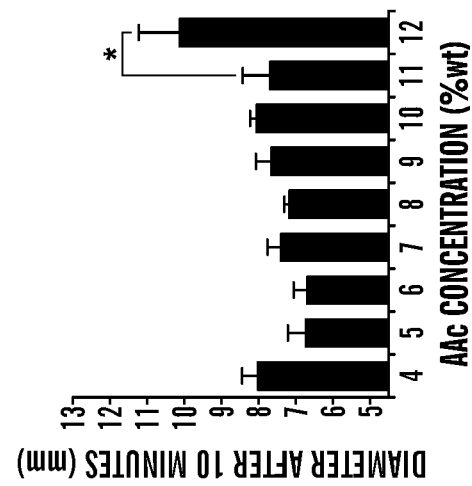
Figure 2B:
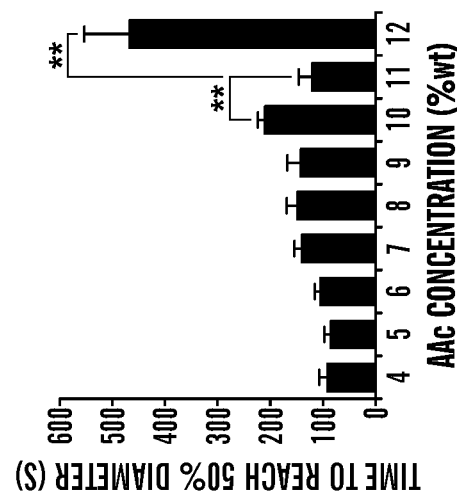
Figure 2D:
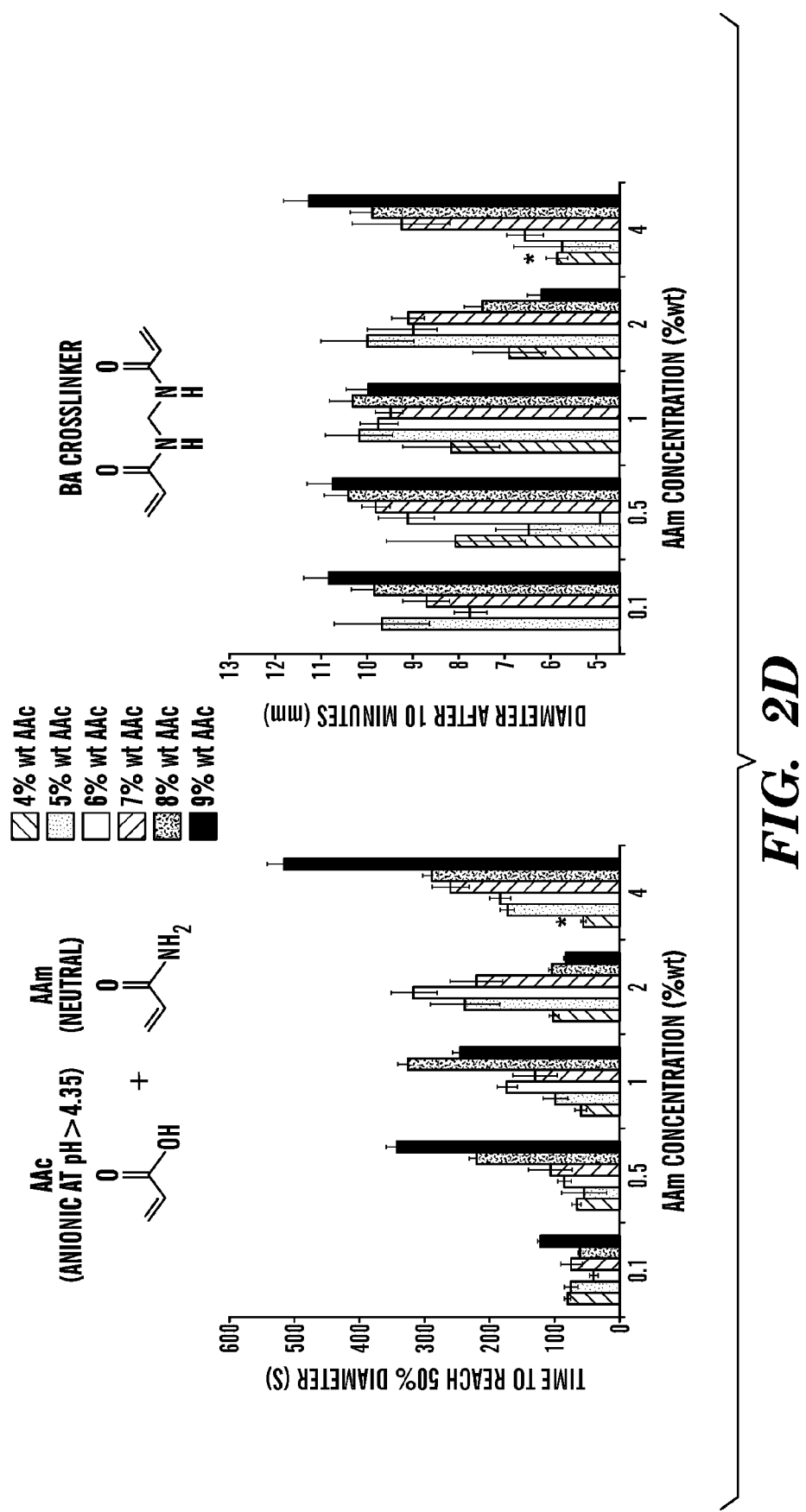

The electro-responsivity of these macroporous gels could be further enhanced by varying the concentration of charged polymer and net hydrogel charge. Gels were formed with different AAc concentrations while holding the bisacrylamide concentration constant at 0.1% wt, and gels composed of higher AAc concentrations generally collapsed slower and to a lesser extent (FIG. 2A). However, quantification of the rate (FIG. 2B) and extent (FIG. 2C) of collapse revealed they did not monotonically vary with AAc concentration. For the 11% wt AAc gels, in particular, the rate of collapse significantly deviated from the trend. This likely resulted from the opposing effects of increasing the AAc concentration, in that it is expected to both (i) enhance responsivity by increasing the amount of charge in the gel (and therefore the amount of electromotive force exerted on the gel) (ii) reduce responsivity by increasing gel stiffness and impeding the movement of ions and water through the gel, and (iii) reduce responsively by increasing the number of counterions required to translocate. Gels formed at 11% AAc likely balanced these three competing parameters to form a highly responsive gel. To examine the impact of polymer concentration independently of hydrogel charge content, cryogels were formed with both charged (AAc) and uncharged (AAm) monomers. The rate (FIG. 2D, left graph) and extent (FIG. 2D, right graph) of gel collapse over a wide range of AAc and AAm concentrations varied greatly. Note that while holding the AAm concentration constant, increasing the AAc concentration increases both the total polymer concentration and the hydrogel charge content. Just as observed with pure AAc gels (FIGS. 2B and 2C), at certain AAc concentrations the rate and degree of electrical collapse was optimized (FIG. 2D, indicated by ‡ at local minima), likely again through a balance of polymer concentration and charge content. Certain gel compositions exhibited better rates and degrees of collapse than the most responsive pure AAc gels (11%), as indicated by asterisks (FIG. 2D). One gel formulation (the 4% wt AAc, 4% wt AAm gel) outperformed the 11% wt AAc (0% AAm) gels in a statistically significant manner in regards to both rate and degree of collapse. Surprisingly, the 4% wt AAc, 4% wt AAm gels (containing ~50% charged monomer, polymeric charge density of 0.007 e Da$^{-1}$) were more responsive than gels composed of lower charge densities. Without wishing to be bound by a theory, this can be attributed to two possible phenomena: (i) utilization of more charged monomer increases the amount of counterions that need to be displaced before the gel can undergo volumetric collapse and (ii) an extremely high charge density along the polymer backbone results in more electrostatic repulsion between polymer chains, thereby impeding collapse. Indeed, previous studies have demonstrated electro-collapsibility using polymeric charge densities lower than those of purely poly (AAc). AAc-co-AAm gels with a reported 20% charge along the polymer (0.0028 e Da$^{-1}$) were capable of extensive collapse (500-fold) but collapsed very slowly, likely due to their nanoporosity.[5] Relatively high temporal responsivities were reported (60% collapse in 30 minutes) when using nanoporous hyaluronic acid (HA) gels[7] (0.0026 e Da$^{-1}$).

Characterization of electro-responsivity in terms of drug release efficiency using gels with different ratios of Alginate (Alg) to poly(AAc) demonstrated that pure alginate gels (10% wt, 0.0057 e Da$^{-1}$) were least responsive, 7/3 wt/wt Alg/AAc gels (0.0082 e Da$^{-1}$) were more responsive, and 5/5 wt/wt Alg/AAc gels (0.01 e Da$^{-1}$) were most responsive. It was not determined if charge densities higher than 0.01 e/Da resulted in improved responsivites (purely AAc gels have 0.0139 e Da$^{-1}$). These studies combined with inventors' discovery indicate that a certain degree of charge is required for efficient electro-mutability, but beyond a certain charge density, electro-responsivity may be impeded.

Figure 3A:
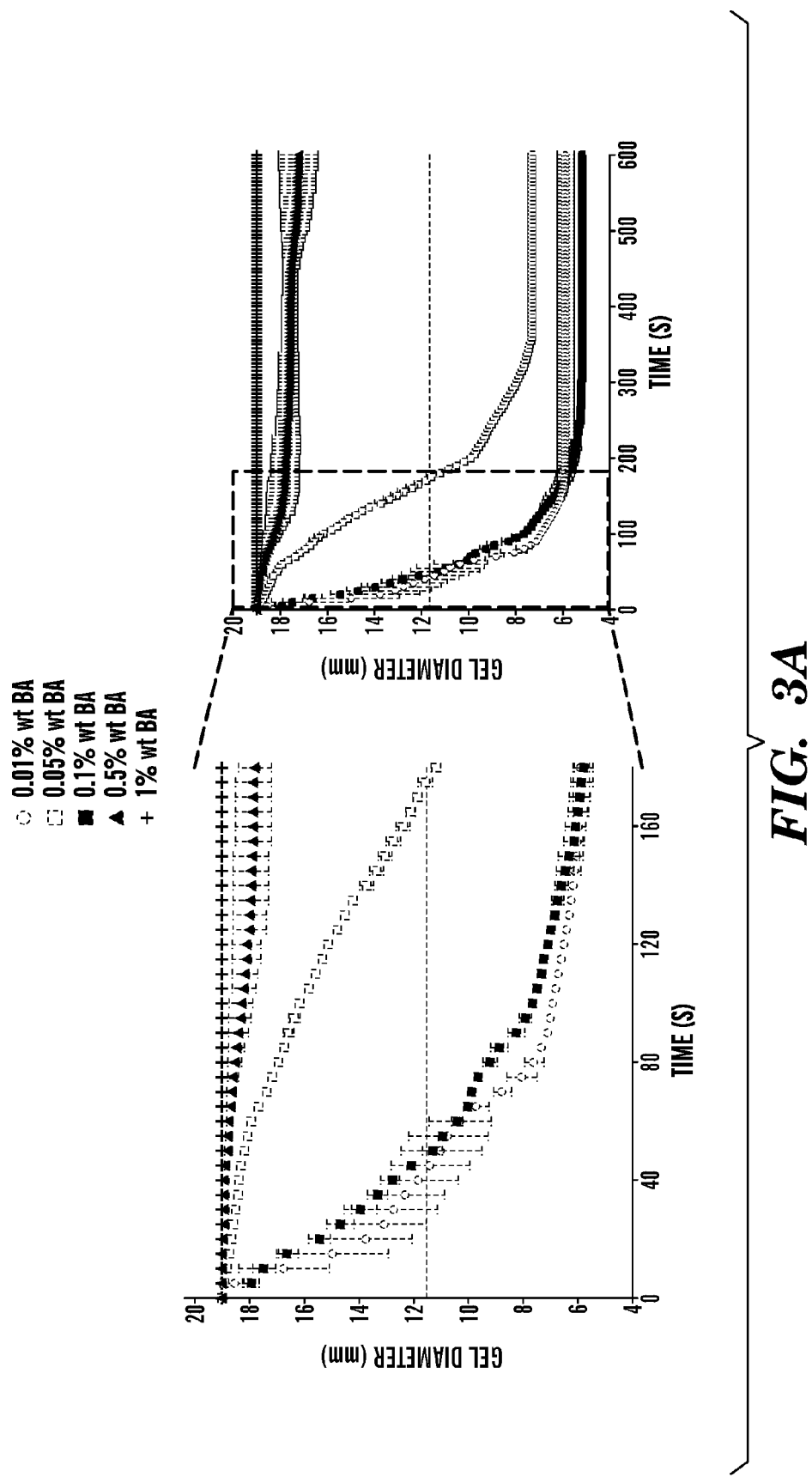
Figure 3B:
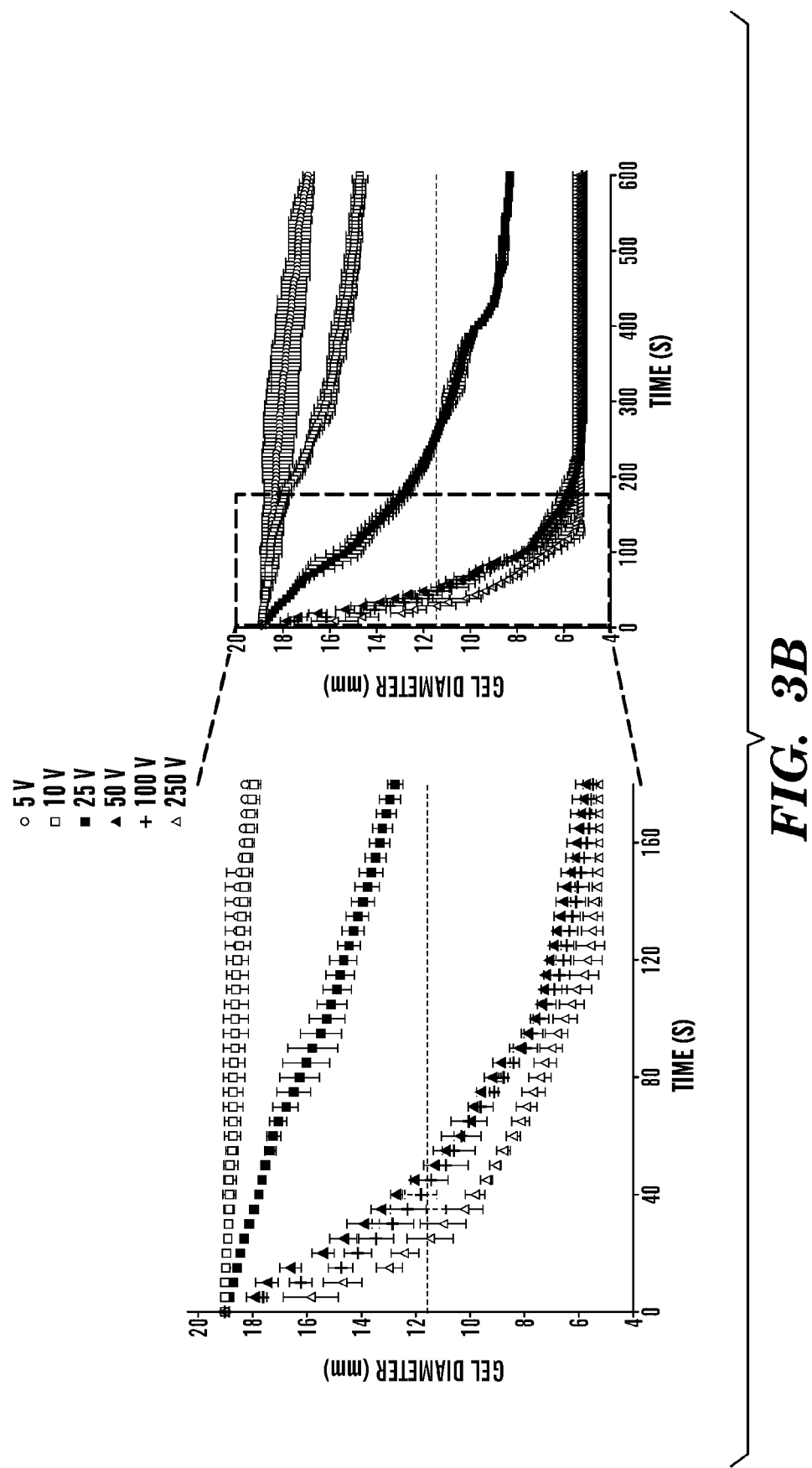

The crosslinking density and the intensity of electrical stimulation had a dramatic impact on the dynamics of gel collapse. More highly cross-linked 4% wt AAc, 4% wt AAm gels had limited electro-responsivity, while gels with lower crosslinking densities collapsed faster and generally to a greater extent (FIG. 3A). It has been shown previously that electro-responsivity is reduced at higher crosslinking ratios.[14] In contrast, the 0.01% and 0.1% wt BA gels disclosed herein performed similarly. While the 0.01% and 0.1% wt BA gels disclosed herein performed similarly, the 0.1% wt BA cross-linked gels were used in subsequent experiments since the 0.01% wt BA gels often fragmented when handled. Application of higher voltages to the gels resulted in faster rates of collapse (FIG. 3B), as seen in other reports.[15] However, increasing the voltage beyond 50 V only moderately enhanced the rate of collapse, suggesting that voltages lower than 50 V can be optimal, from the perspective of lower power consumption, less electrolysis, and the ability to regulate the rate of collapse in a voltage-proportioned manner. The proportioned but non-linear relationship between applied electrical stimulus and responsivity has been reported elsewhere.[16]

The level of electro-responsivity provided by the 4% wt AAc, 4% wt AAm, 0.1% wt BA cryogels when stimulated using 50 V was a marked improvement over the responsivity of similarly sized electrically collapsible hydrogels described in the art. There have been several reports of similar or better electro-responsivites in micro-scale gels[6] and when characterizing responsivity based on hydrogel bending[17,18,19]. However, when comparing to gels of a similar size that experienced large-scale, voltage-dependent volumetric collapse, cryogels described herein were 40[7] to 2000[5] fold more electro-responsive. The performance of micro-scale gels could likely also be dramatically improved with the approach taken here. The ability of the electrogels described in this report to collapse so much more efficiently under electrical stimulus is likely a product of (i) a balanced charged to uncharged polymer ratio, (ii) a particularly organized and planar macroporous structure (FIG. 1A), (iii) a relatively high pore interconnectivity (FIG. 1C), and (iv) a relatively low modulus (FIG. 1B).

These highly electro-responsive, macroporous gels were easily integrated into an optical array capable of configurational and chromatic modulation. Gels were created that contained pigmented polystyrene beads and were placed in an array format (FIG. 3C). This array of individually collapsible, pigment-containing gels was inspired by cephalopods, which are capable of modulating the optical profile of their skins using an array of collapsible pigment sacks called chromatophores.[20] Using this simple pigment sack configuration, cephalopods are able to rapidly camouflage themselves, optically blending into environments with both chromatic and textural complexities.[21] In our synthetic array, this optical adaptability was achieved simply by turning on the voltages addressed to particular gels. Both configurational ("H" in FIG. 3C, top row) and chromatic (transition from red-blue-yellow to a primarily blue field in FIG. 3C, bottom row) changes could be readily achieved. While these arrays do not achieve the spatiotemporal resolution provided by commercial optical display technologies (e.g., liquid crystal displays, plasma displays, cathode ray tubes), they do provide a means by which simple optical modulations can be achieved with hydrogels in aqueous environment using low amounts of energy, and unsophisticated and inexpensive electronics. This approach can be useful as adaptive camouflage, particularly in wet environments. A limitation, however, is that these gels take hours to re-swell back to their original size.

Figure 4A:
FIGS. 4A-4E show cryogels composed of polyelectrolytic, biocompatible polymer exhibit electro-responsivity and are capable of delivering drugs in a voltage-triggered manner.
Figure 4A:
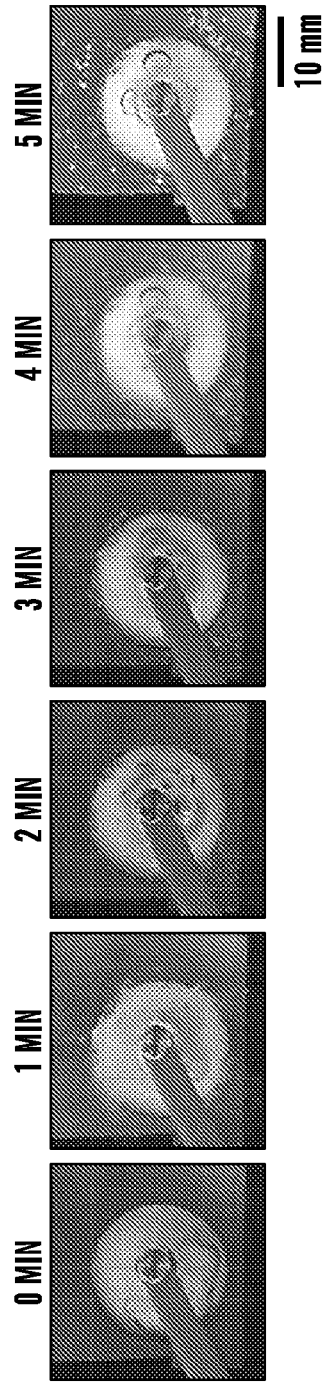
Figure 4B:
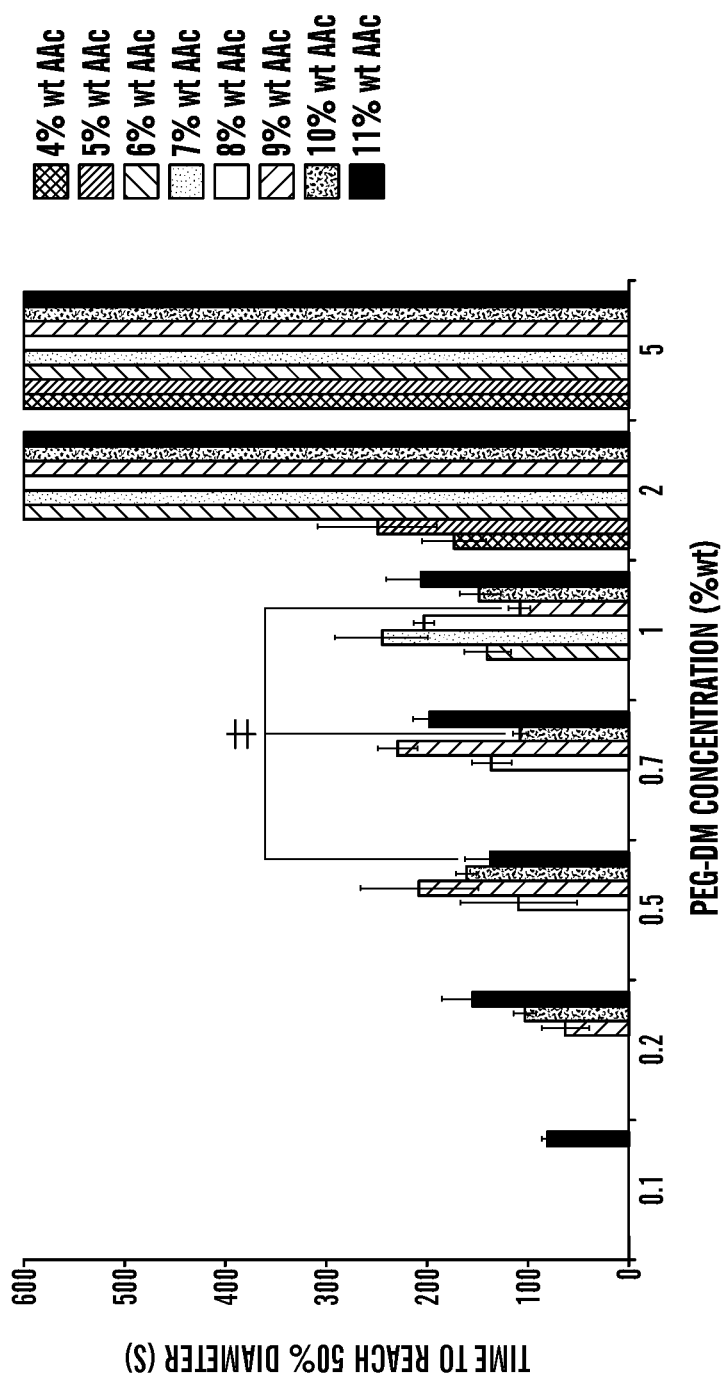
Figure 4C:
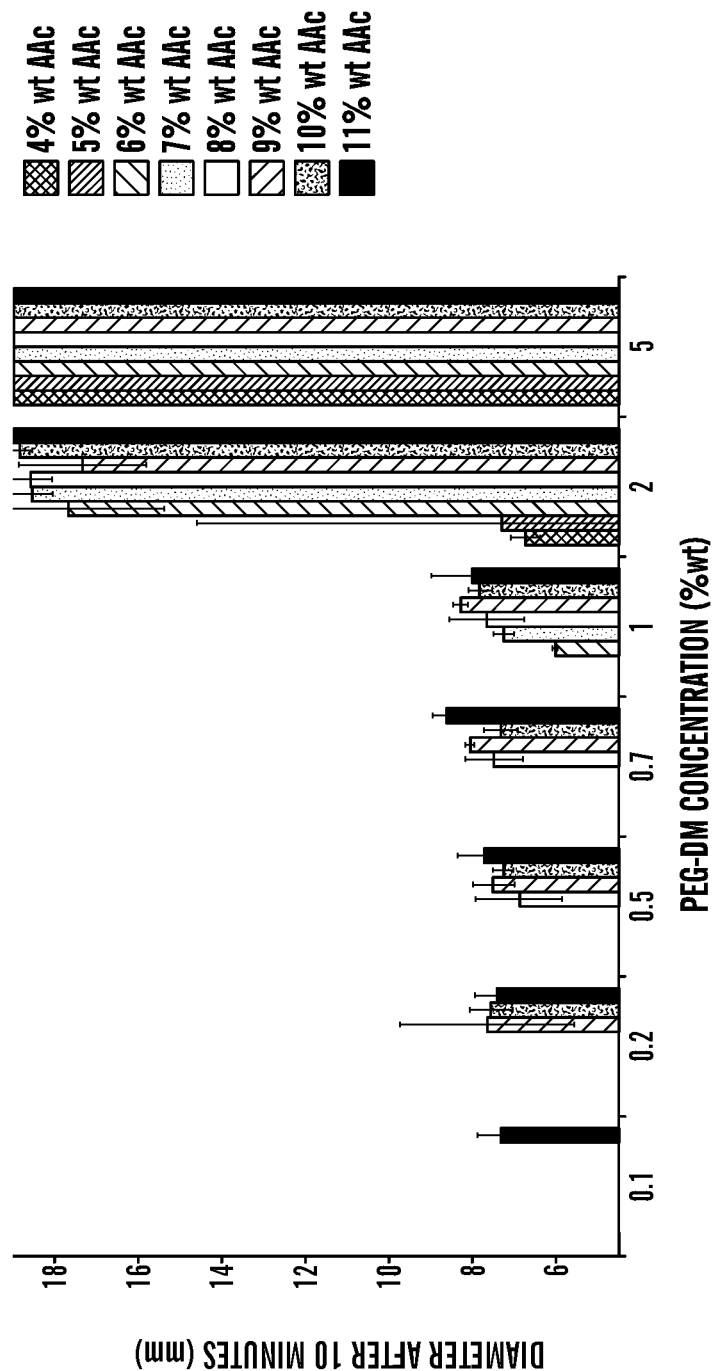
Figure 4D:
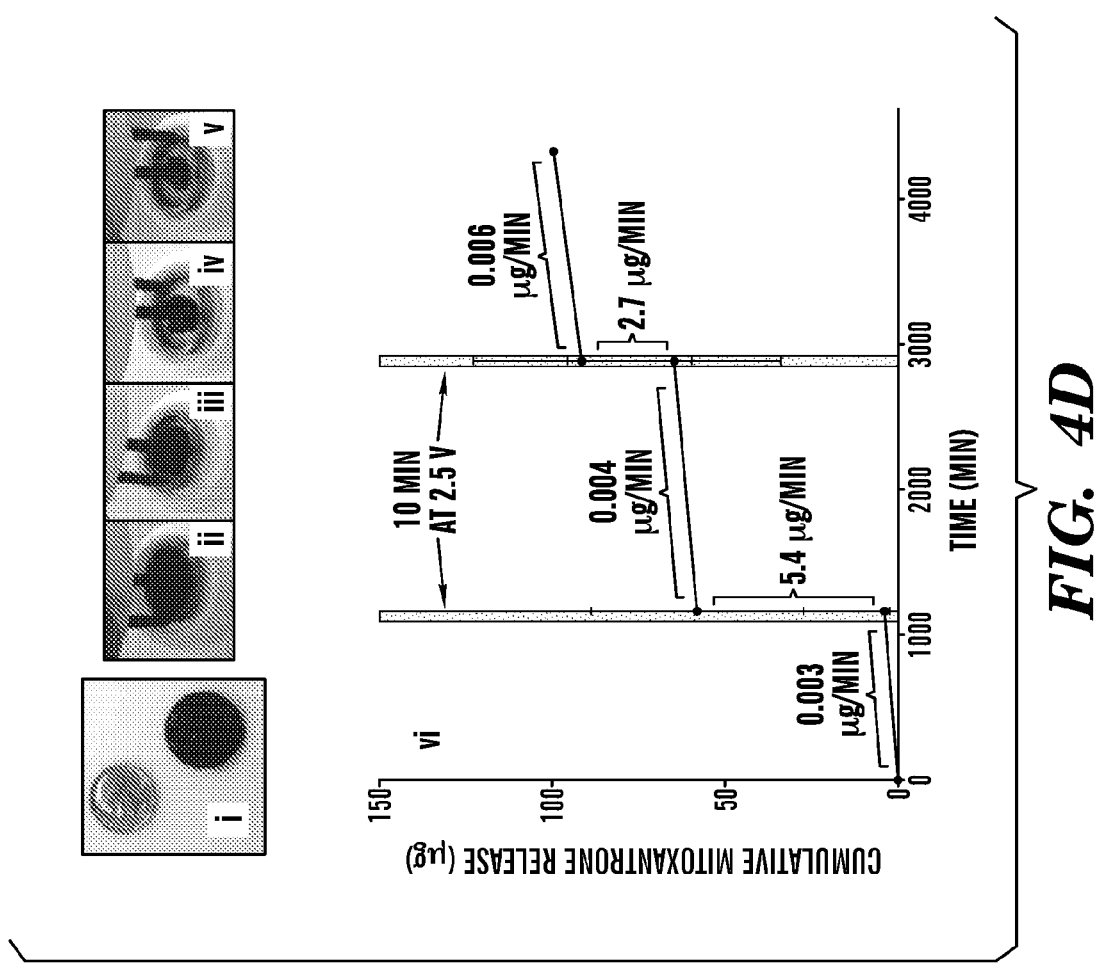
Figure 7:
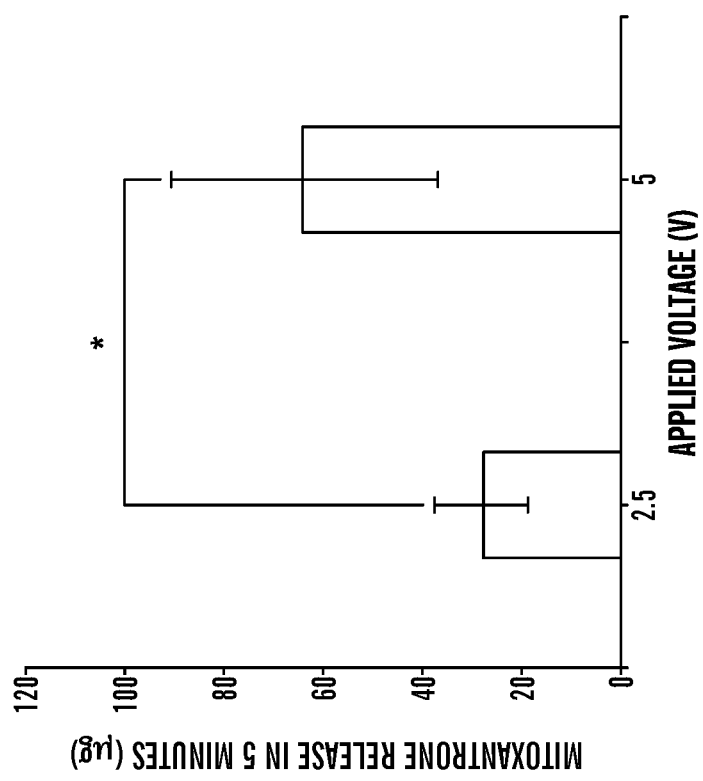
FIG. 7 shows that drug release is regulated by applied voltage. The cumulative amounts of mitoxantrone released during 5 minutes of electrical stimulation in PBS as a function of applied voltage. Values represent mean and standard deviation (N=4) and * indicates $p \le 0.05$.
Figure 8:
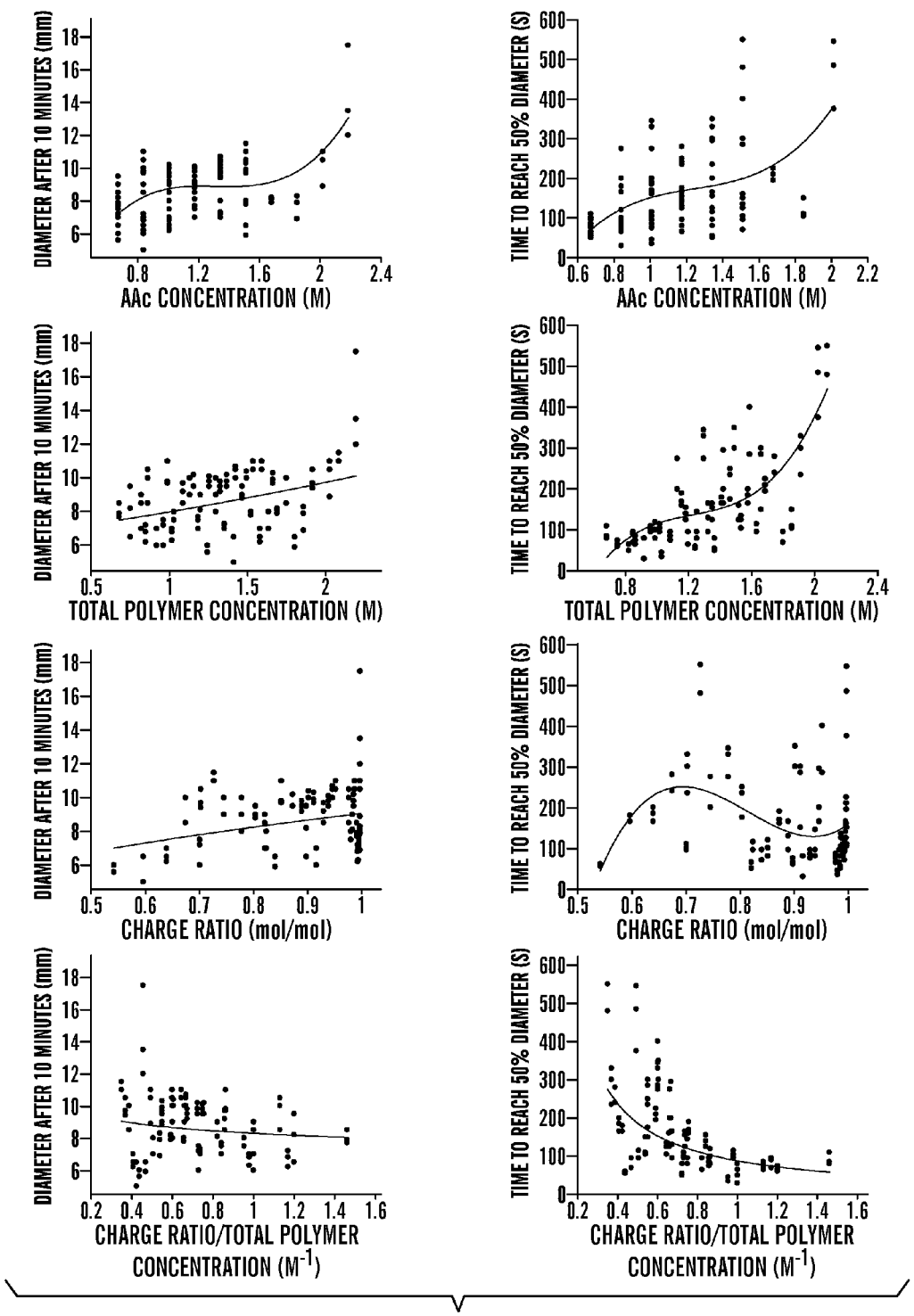
FIG. 8 shows an analysis of parameters associated with gel makeup reveals that the percent of charged species in the gel divided by the total polymer concentration is a good predictor of the degree and rate of collapse. Gel diameters after 10 minutes (left column) and the time it takes to reach half diameter (right column) as a function of: AAc concentration (top row); total polymer concentration regardless of charge ($2^{nd}$ row); charge ratio as defined by the number of charged monomers over the total number of monomers ($3^{rd}$ row); and, the charge ratio over the total polymer concentration (bottom row). The charge ratio over the total polymer concentration appears to be a good predictor of gel collapsibility. This is consistent with the idea that gel collapsibility should be proportional to the charge density within the gel (allowing for increased electromotive forces when exposed to an electric field) while inversely proportional to the amount of total polymer (more polymer is more difficult to move at a given amount of electromotive force).

Rapidly collapsible electro-responsive gels could also be made from biologically friendly materials, and were capable of efficiently harboring and delivering drugs when electrically stimulated in biological media. Macroporous gels containing AAc and crosslinked with 5 kDa poly(ethylene glycol)dimethacrylate (PEG-DM) were cryogelated, and exhibited the ability to electrically collapse (FIG. 4A). The amount of anionic AAc and PEG-DM crosslinker used to form these electrogels had a deterministic effect on the rate (FIG. 4B) and extent (FIG. 4C) of electrical collapse. As observed in AAc-co-AAm gels (FIGS. 2B, 2C, and 2D), increasing the amount of AAc—and therefore both the overall polymer concentration and total charge content—resulted in local minima at distinct AAc concentrations where polymer concentration and charge content were likely optimally balanced (indicated by ‡ in FIG. 4B). Out of these three gels, the 9% wt AAc, 1% wt PEG-DM gels were easiest to handle and did not fragment during preparation for experiments. These gels were loaded with mitoxantrone (FIG. 4D, i)—an anthracenedion, antineoplastic drug used in the treatment of metastatic breast cancer, acute myeloid leukemia, non-Hodgkin's lymphoma,[22] and multiple sclerosis.[23] When not stimulated, these gels effectively retained drug, releasing drug at a rate of between 0.003-0.006 µg per minute (FIG. 4D, vi). This corresponds to only 0.9-1.7% of the encapsulated drug being released per day. Subjecting gels held in phosphate buffered saline (PBS) to 2.5 V over the course of 15 minutes led to gel collapse (FIG. 4D, ii-v). When gels were stimulated using two 2.5 V pulses lasting 10 minutes each (1-4 V cm$^{-1}$ E-field, drawing <5 mW power), the drug delivery rate was enhanced by 450- to 1800-fold, with release rates ranging from 2.7-5.4 µg min$^{-1}$ (5.4-10.8% of encapsulated drug released in only 10 minutes). Furthermore, the drug delivery rate could roughly be doubled by increasing the applied voltage two-fold, resulting in a 1300- to 6000-fold enhancement in drug delivery rate (FIG. 7). Compared to previously reported electrically collapsible drug delivery hydrogels,[13-15, 24-25] the cryogels described herein provided heightened performance, particularly in terms of the degree to which drug release was enhanced when electrically stimulated (1000s-fold vs. two- to five-fold[13-15, 24-25] enhancement). The dramatic increase in drug release rate was likely due to both convective (via volumetric collapse) and electrophoretic (electrically stripping drug away from the scaffold) mechanisms, while the excellent retention was likely due to drug-scaffold electrostatic affinity. Affinity-based drug approaches from hydrogels have previously proven to provide a means by which the drug delivery profile can be tuned a priori while using gel fabrication techniques that preserved macromolecular bioactivity.[26] Our approach expands upon these advantages by additionally providing on-demand, stimuli-proportioned control.

Figure 4E:
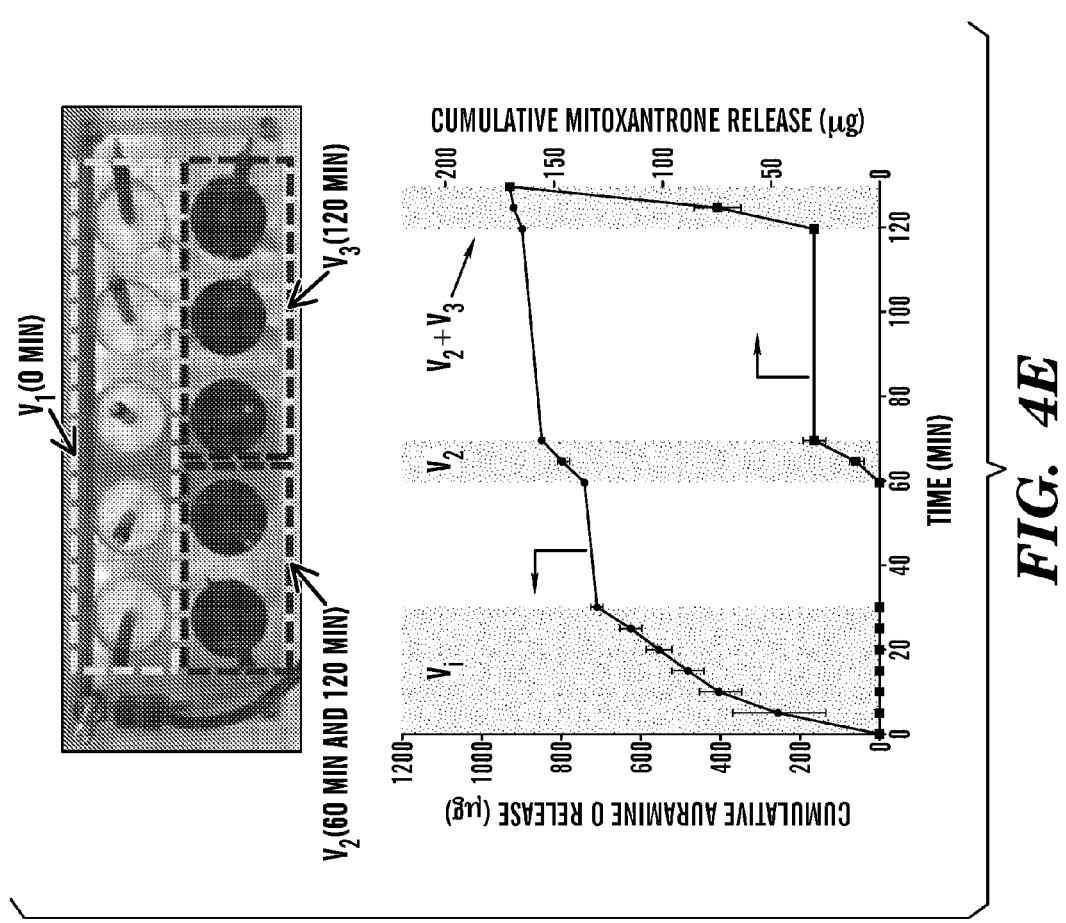

Complex delivery profiles of multiple drugs were achieved by integrating these drug-containing gels into an array format. In a 10-gel array (FIG. 4E, top image), five gels containing Auramine O were assigned to voltage $v_1$ and triggered from 0-30 minutes. Two gels containing mitoxantrone were assigned to $v_2$, and triggered from 60-70 minutes and then again from 120-130 minutes. The remaining three mitoxantrone-loaded gels were assigned to $v_3$ and triggered from 120-130 min. The timing and rate of release for both drugs was controlled by the timing and location of voltage applied to the distinct voltage addresses (FIG. 4E, bottom graph). An initial burst of Auramine O (i; 0 to 30 minutes) was obtained by triggering the five gels containing this drug to collapse over this time frame. A subsequent period during which no voltage was applied to any gels (ii; 30 to 60 minutes) resulted in little drug release. Subsequently triggering the two gels assigned to $v_2$ (iii; 60-70 minutes), resulted in a small burst in mitoxantrone release. A period of little drug release (iv; 70 to 120 minutes) again followed, during which no voltage was applied. Finally, a relatively large burst in mitoxantrone release was obtained by simultaneously triggering the second collapse of the two gels assigned to $v_2$, and the collapse of the last set of gels assigned to $v_3$ (v; 120 to 130 minutes). The slight amounts of Auramine O release in the second and third drug delivery phases are likely a result of Auramine O's weaker electrostatic interaction with the poly(AAc) matrix. The act of retrieving the sample from and adding fresh PBS to the device results in a small amount of Auramine O release. Reservoir-based, microchip drug delivery arrays have been used to similarly coordinate the delivery of multiple drugs;[27] however, these microchip-based systems assume very different physical forms than the system described here. Additionally, the recent demonstration that drug release can be triggered using a wireless system in human subjects[28] supports the potential utility of electrically responsive cryogels. While previously described reservoir systems have enormous potential, they have not demonstrated the ability to coordinate the delivery rate of multiple drugs through stimuli proportioned control, but instead demonstrate all or nothing release from a reservoir. The system we have shown here is capable of stimuli proportioned regulation (FIG. 7). This ability to coordinate the release rates of multiple drugs may be crucial in applications such as detoxification, pain relief, vaccination, infection combat, cancer treatment, diabetes treatment, the treatment of degenerative diseases (e.g., Alzheimer's and Parkinson's diseases), tissue engineering, and even in non-biomedical areas.[29] These arrayed electrically responsive hydrogels may also aid in understanding and better controlling the highly choreographed sequence of events associated with tissue development and regeneration.[30]

The inventors have created porous polyelectrolytic hydrogels made using an inexpensive, straightforward, and scalable process, and exhibited dramatically improved electro-responsivity in terms of the rate, degree and quality of volumetric collapse. These cryogels can be made through normal extrusion and molding processes in aqueous media; they need be merely frozen during gelation. The inventors have demonstrated that these cryogels are capable of (i) rapid electrical collapse (in tens of seconds), (ii) extensive electrical collapse (down to less than 5% of their original area, (iii) high quality of electrical collapse (cryogels remain intact), (iv) precisely timed and organized control through inexpensive and unsophisticated means, (v) being composed of biologically friendly materials while retaining highly electro-responsive profiles, and (vi) harboring and delivering drugs in a triggered and stimulus-proportioned manner.

These cryogels electrically collapsed 63% in 25 seconds and 93% in 150s, corresponding to a 40-2000 fold improvement over previous reports. Electrogels were easily integrated into arrays capable of simple and rapid configurational and chromatic optical modulations, and when loaded with drugs, were able to coordinate the release profile of multiple drugs with great flexibility. Further, they exhibited efficient stimulated delivery (6000-fold increase in delivery rate at 5 V). Enhanced performance of these electrogels will likely expand their utility in optics and drug delivery and will facilitate their use in a variety of other emerging technologies.

Materials and Methods

Hydrogel and cryogel preparation: To form nanoporous PAAc-co-AAm hydrogels, depending on hydrogel composition, different amounts of Acrylic Acid (AAc), Acrylamide (AAm), NaOH (at 465 μg per mg of AAc), Bisacrylamide (BA), deionized water, and pigment (methacrylated rhodamine or polystyrene beads) were mixed by vortexing. Then, Tetramethylethylenediamine (TEMED) and Ammonium Persulfate (APS) redox reagents were added and the solution was transferred to room-temperature Teflon molds (¾ inch diameter, 2 mm thick) for gelation in 600 μl aliquots. After 1 hour, hydrogels were transferred to deionized water and allowed to fully swell overnight. They were rinsed three times in deionized water and cut to 19 mm diameter disks prior to experimentation. All chemicals, reagents and polymers were purchased from Sigma-Aldrich Corp., St. Louis Mo., USA.

PAAc-co-AAm cryogels were formed in a similar fashion except using frozen Teflon molds. After mixing and addition of redox reagents, cryogel precursor solutions were transferred to frozen Teflon molds in a −20° C. freezer and left to gel at −20° C. overnight (see FIG. 5A for an illustration of the cryogelation process). They were then removed from the freezer, thawed, and transferred to a petri dish containing deionized water where they were allowed to fully swell for one day. They were rinsed three times in deionized water and cut to 19 mm diameter disks prior to experimentation.

PAAc-co-PEGDM cryogels were fabricated in a similar manner as the PAAc-co-AAm cryogels. For drug delivery experiments, after cryopolymerization, they were removed from the freezer, thawed and allowed to swell overnight in Phosphate Buffered Saline (PBS) containing 1 mg ml$^{-1}$ of drug (i.e., either mitoxantrone or Auramine O). They were cut to 19 mm diameter disks and rinsed in PBS once prior to experimentation.

Figure 5C:
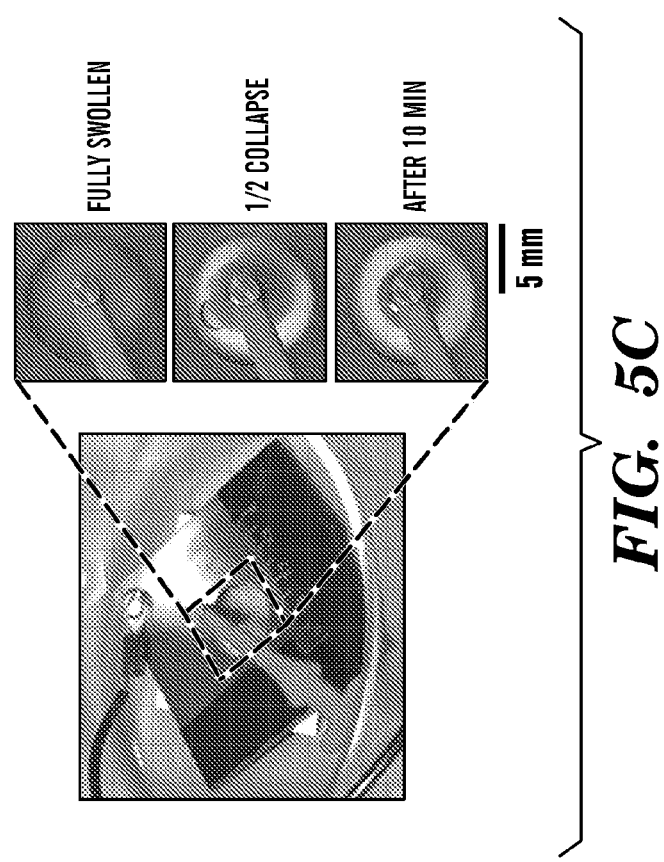
Figure 5B:
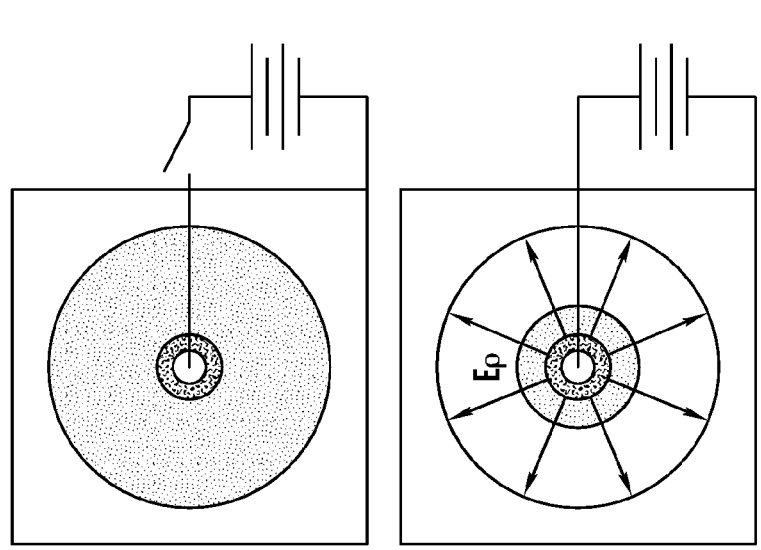

Evaluation of Electro-Responsivity:

Nanoporous hydrogels and macroporous cryogels (19 mm diameter disks) were transferred to a custom electric-field exposure device (schematic and photographs in FIGS. 5B and 5C). This device exposed the hydrogel samples to outward radial electric fields (FIG. 5B) that were proportional in magnitude to the voltages applied across the device's stainless steel electrodes. The gels were submerged in 150 mL of either deionized water or PBS, depending on the experiment. A voltage source was connected to the electrodes that was capable of providing up to 1000 VDC. Gel diameters during the course of 10 minute experiments were monitored (FIG. 5C). Photographs were taken from a stationary camera and these photographs were used to either (i) plot the hydrogel diameter vs. time, (ii) determine the time at which gel diameter becomes 50% of its original diameter (FIG. 5C, middle right image), and/or (iii) determine the hydrogel diameter at 10 minutes (FIG. 5C, bottom right image).

Evaluation of Drug Release:

For experiments where mitoxantrone release was quantified, custom vials were made from Teflon, where 19 mm diameter gels could be exposed to voltages while being submerged in 15 ml of PBS (FIG. 4D, i-v). During drug release studies, samples of the PBS/drug could be removed from the vials intermittently and analyzed for mitoxantrone content. This was done by measuring optical absorbance of the samples at 610 nm and using a linear regression standard curve generated with known drug quantities to correlate the amount of optical absorbance to mitoxantrone concentration values.

In experiments where multiple drugs were released from 10-gel arrays, a custom array-formatted device (FIG. 4E) was made from Teflon, where ten 19 mm diameter gels could be exposed to ten independent voltages, allowing gels to be triggered individually or in concert. All ten gels were submerged in 50 ml of PBS. During experimentation, gels would release their drug into the same 50 mL PBS basin. Samples of PBS/drug could be removed from the device's basin intermittently and analyzed for mitoxantron and auramine O content simultaneously. This was done by measuring optical absorbances at 610 nm (corrected at 640 nm) for mitoxantrone and 410 nm (corrected at 370 nm) for auramine O. Individual mitoxantrone and auramine O standard curves were used to correlate the optical absorbances at 610 nm and 410 nm to mitoxantrone and auramine O concentrations, respectively.

Sample Preparation for X-Ray Microtomography Imaging:

Barium Sulfate (BaSO$_4$) was used as a contrast enhancer for x-ray microtomography (μCT) imaging. After gelation or cryogelation, hydrogels were allowed to swell for 3 days in a 50% wt BaSO$_4$ and deionized water mixture under constant but light stirring. This allowed for the gels to fully swell and remain hydrated while concentrated BaSO$_4$ filled any macropore space that may have been present in the samples. Therefore, when imaged using a X-Tek, HMXST225 μCT x-ray imaging system, macropores appeared as high attenuation "white" spots whereas hydrogel space appeared as low attenuation "dark" space. Inverse images for the 2D and 3D images are provided in FIG. 1a, where pore space is represented by black space in 2D renderings and open uncoloured space in 3D renderings.

Sample Preparation for Scanning Electron Imaging:

For scanning electron microscopy (SEM) images of cryogels before and after electrical exposure, 4% wt AAc, 4% wt AAm, 0.1% wt BA cryogels were used. The "before" cryogel was cryogelated, thawed, allowed to swell overnight, and rinsed three times in deionized water before being cut along its cross-section and flash-frozen by submersion in liquid nitrogen for 2 minutes. The sample was then lyophilized for 3 days and platinum-palladium sputter-coated. The cross-sectional SEM image was obtained using a Zeiss FESEM Supra55VP.

For "after" SEM images, a 4% wt AAc, 4% wt AAm, 0.1% wt BA cryogel was created and collapsed according to the protocols outlined above using 50 V for 10 minutes. The collapsed cryogel was then quickly cut along its cross-section and flash-frozen by submersion in liquid nitrogen for 2 minutes. It was then lyophilized and sputtercoated and imaged similarly to the "before" sample.

Figure 6A:
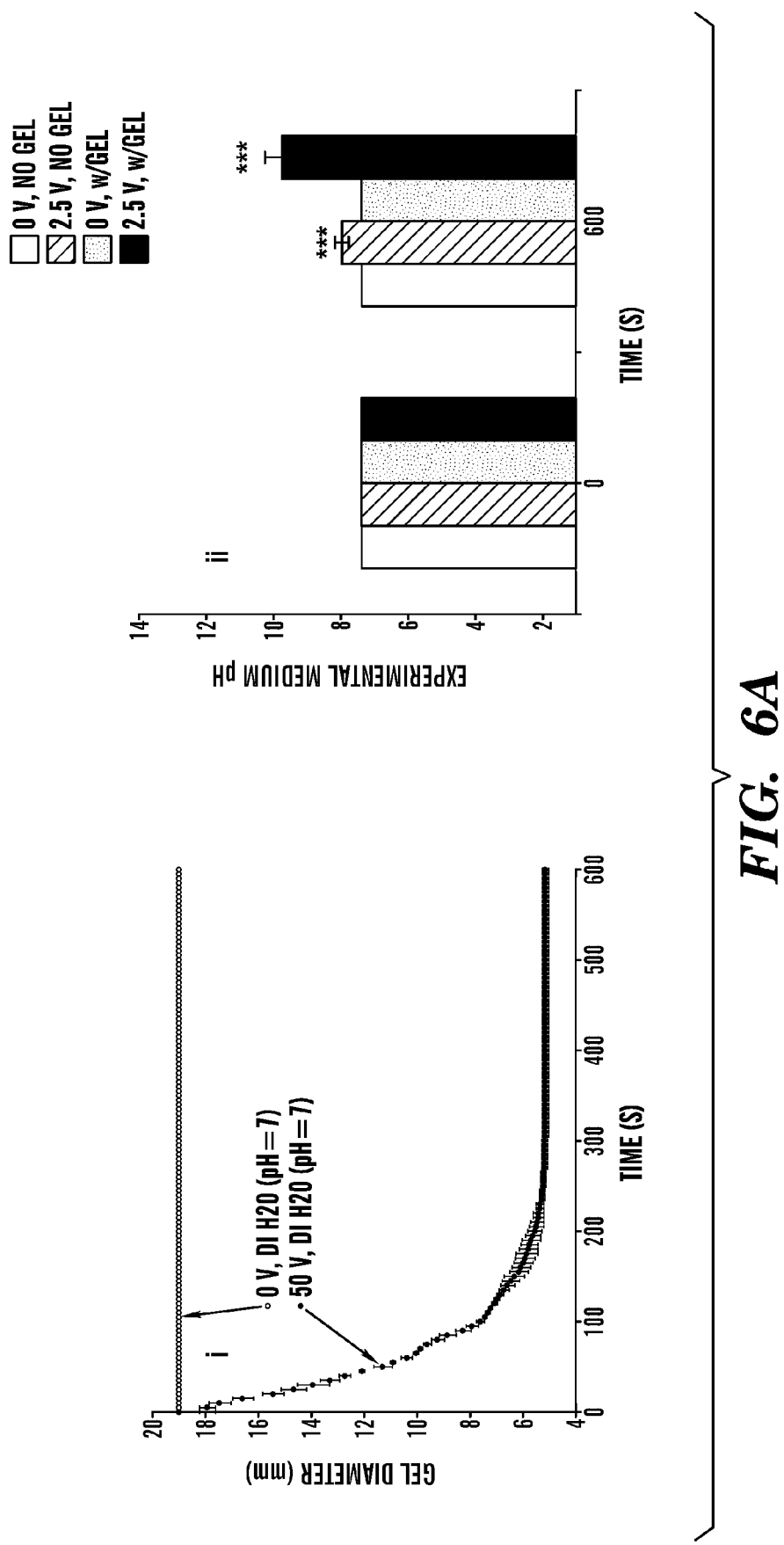
FIGS. 6A through 6C show that electric field exposure is required for rapid and extensive gel collapse while the pH and ionic strength of the experimental media play a secondary role.
Figure 6C:
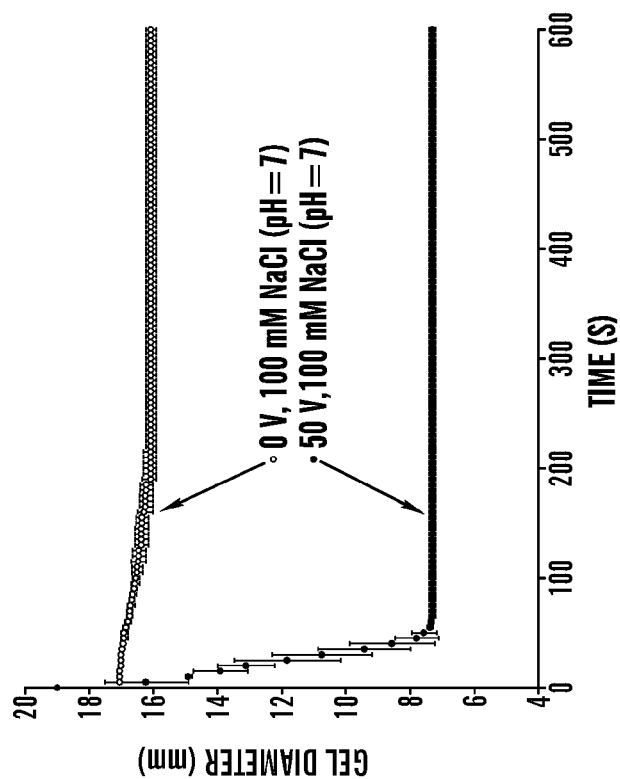
Figure 6B:
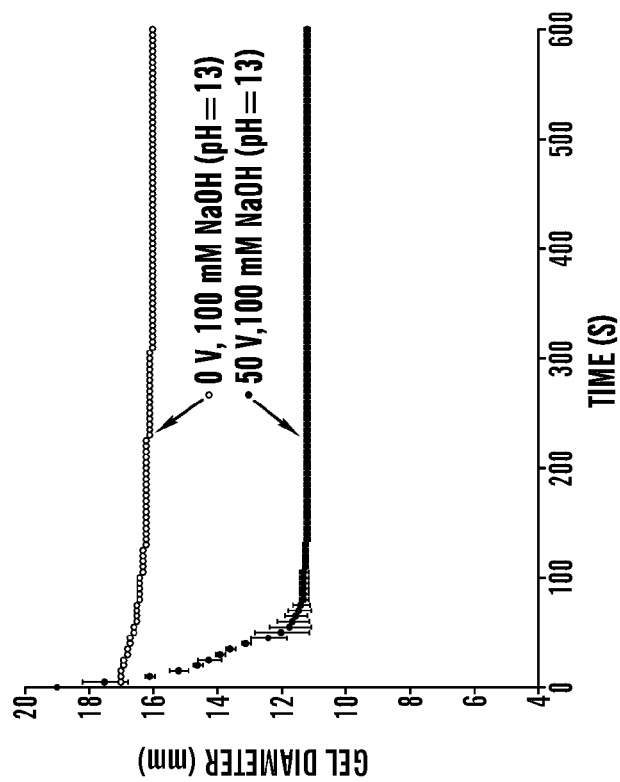

The Respective Roles of Electric Field, pH Changes, and Inoic Strength on Gel Collapse:

The rapid and extensive volumetric collapse observed from the electrogels required electric field exposure, while pH and ionic strength changes played a less significant, secondary role. Determining the roles of pH and ionic strength was important since it was previously shown that both pH and ionic content affected swelling and deswelling of polyelectrolytic hydrogels (P. Calvert, in Electroactive Polymer (EAP) Actuators as Artificial Muscles: Reality, Potential, and Challenges, 2$^{nd}$ Ed. (Ed: Y. Bar-Cohen), SPIE Press, Bellingham, Wash., USA 2004, Ch. 5). When initial pH was set at 7, macroporous gels (4% wt AAc, 4% wt AAm, 0.1% wt BA) collapsed rapidly when exposed to 50 V and did not collapse when unstimulated (FIG. 6A, i). pH did increase from 7 to 10.5 when these gels were exposed to 50 V in deionized water (FIG. 6A, ii). Both voltage and gel presence were required to increase the pH, as that was the only condition that allowed for electrical current and therefore electrolysis at the electrode-medium interface. To determine if this increase in pH was responsible for the rapid and extensive gel collapse, the pH was manually increased to 13 at time t=0 through the addition of NaOH and gel collapse was monitored with and without electrical stimulation (FIG. 6B). Gels not exposed to electric field did begin to collapse starting at time t=0 (FIG. 6B, red curve). However, the rate and degree of collapse was not nearly as fast or extensive as observed under voltage (50 V exposure with initial pH=7, FIG. 6A, i, blue curve). We hypothesized that the slight collapse observed in these gels was a result of the sudden introduction of cations to the media and not necessarily the change in pH. A similar experiment was then run where NaCl was introduced at a molar equivalent level, in lieu of NaOH (FIG. 6C). Indeed, gels that were not exposed to voltage collapsed at similar rates and degrees when submerged in 100 mM NaCl instead of NaOH (compare red curves in FIGS. 6B and 6C). These data indicate that while pH and ionic strength do play roles in gel collapse, electric fields are the primary driving force behind the observed rapid and extensive collapses.

REFERENCES

[1] C. E. D. Chidsey, R. W. Murray, *Science* 1986, 231, 25.
[2] P. Calvert, *MRS Bull.* 2008, 33, 207.
[3] S. Murdan, *J. Control. Release* 2003, 92, 1.
[4] Y. Bar-Cohen, Q. Zhang, *MRS Bull.* 2008, 33, 173.
[5] T. Tanaka, I. Nishio, S. T. Sunm, S. Ueno-Nisho, *Science* 1982, 218, 467.
[6] D. J. Beebe, J. S. Moore, J. M. Bauer, W. Yu, R. H. Liu, C. Devadoss, C. B.-H. Jo, *Nature* 2000, 404, 588.
[7] R. Tomer, D. Dimitrijevic, A. T. Florence, *J. Control. Release* 1995, 33, 405.
[8] K. Sutani, I. Kaetsu, K. Uchida, *Radiat. Phys. Chem.* 2001, 61, 49.
[9] Y. Yang, J. Engberts, *Coll. Surf. A: Physiocochem. Eng. Aspects* 2001, 169, 85.
[10] S. Murdan, *J. Control. Release* 2003, 92, 1.
[11] S. A. Bencherif, W. R. Sands, D. Bhatta, P. Arany, C. Verbeke, D. A. Edwards, D. J. Mooney, *Proc. Natl. Acad. Sci. USA* 2012, 109, 19590.
[12] A. Kumar, A. Srivastava, *Nat. Protoc.* 2010, 5, 1737.
[13] S. H. Yuk, S. Cho, H. B. Lee, *Pharm. Res.* 1992, 9, 995.
[14] N. Paradee, A. Sirivat, S. Naiamlang, W. Prissanroon-Ouajai, *J. Mater. Sci: Mater. Med.* 2012, 23, 999.
[15] K. Sawahata, M. Hara, H. Yasunaga, Y. Osada, *J. Control. Release* 1990, 14, 253.
[16] C. Kwon, Y. H. Bae, T. Okano, S. W. Kim, *J. Control. Release* 1991, 17, 149.
[17] Y. Osada, H. Okuzaki, H. Hori, *Nature* 1992, 355, 242.
[18] M. L. O'Grady P. Kuo, K. K. Parker, *ACS Appl. Mater. Interfaces* 2010, 2, 343.
[19] T. Shiga, T. Kurauchi, *J. Appl. Polym. Sci.* 1990, 39, 2305.
[20] L. M. Mäthger, R. T. Hanlon, *Cell Tissue Res.* 2007, 329, 179.
[21] R. T. Hanlon, C. C. Chiao, L. M. Mathger, K. C. Buresch, A. Barbosa, J. J. Allen, L. Siemann, C. Chubb, in *Animal camouflage: mechanisms and functions*. (Eds: M. Stevens, S. Merilaita), Cambridge University Press, Cambridge, United Kingdom 2011, Ch. 9.
[22] C. Parker, R. Waters, C. Leighton, J. Hancock, R. Sutton, A. V. Moorman, P. Ancliff, M. Morgan, N. Goulden, N. Green, T. Révész, P. Darbyshire, S. Love, V. Saha, *Lancet* 2010, 376, 2009.
[23] E. Fox, *Clin. Ther.* 2006, 28, 461.
[24] S. Niamlang, A. Sirivat, *Int. J. Pharm.* 2009, 371, 126.
[25] K. Juntanon, S. Niamlang, R. Rujiravanit, A. Sirivat, *Int. J. Pharm.* 2008, 356, 1.
[26] K. Vulic, M. S. Shoichet, *J. Am. Chem. Soc.* 2012, 134, 882.
[27] J. T. Santini, M. J. Cima, R. A. Langer, *Nature* 1999, 397.
[28] R. Farra, N. F. Sheppard, L. McCabe, R. M. Neer, J. M. Anderson, J. T. Santini, M. J. Cima, R. A. Langer, *Sci. Transl. Med.* 2012, 4, 1.
[29] R. A. Langer, *Science* 1990, 249, 1527.
[30] W. M. Reichert, B. D. Ranter, J. Anderson, A. Coury, A. S. Hoffman, C. T. Laurencin, D. Tirrell, *J. Biomed. Mater Res. Part A* 2010, 96, 275.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

What is claimed is:

1. A macroporous electro-responsive cryogel,
comprising charged monomers and cross-linker monomers in a ratio of about 8:1 to about 7:0.5 or a ratio of about 8:0.5 to about 40:1 by weight, volume or mole,
wherein the cryogel is prepared by polymerizing an aqueous solution of the charged monomers and the cross-linker monomers by freezing at a temperature below the freezing temperature of the aqueous solvent,
wherein the charged monomers are about 4% to about 11% by weight, volume or mol of the aqueous solution, and
wherein the cryogel is capable of volumetric collapse in response to an electrical stimulus.

2. The macroporous electro-responsive cryogel of claim 1, wherein the charged monomers are selected from the group consisting of acrylic acid (AAc), methacrylic acid, 3-(acrylamido)phenylboronic acid and derivatives, and any combinations thereof.

3. The macroporous electro-responsive cryogel of claim 1, wherein the cross-linker monomers are selected from the group consisting of N,N'-methylenebis-acrylamide (BA), polyethyleneglycol di(meth)acrylate (PEG-DM), and any combination thereof.

4. The macroporous electro-responsive cryogel of claim 1, wherein the charged monomers are acrylic acid and the cross-linker monomers are N,N'-methylenebis-acrylamide or polyethyleneglycol di(meth)acrylate.

5. The macroporous electro-responsive cryogel of claim 1, wherein the charged monomers are about 4% to about 9% by weight, volume or mol of the aqueous solution.

6. The macroporous electro-responsive cryogel of claim 1, wherein the cross-linker monomers are from 0.01% to 10% by weight, volume or mol of the aqueous solution.

7. The macroporous electro-responsive cryogel of claim 1, wherein the aqueous solution further comprises uncharged monomers.

8. The macroporous electro-responsive cryogel of claim 7, wherein the uncharged monomers are selected from the group consisting of N-substituted and non-substituted acrylamides; N-substituted and non-substituted (meth)acrylamides; N-alkyl substituted N-vinylamides; Hydroxyalkyl (meth)acrylates; vinylacetate; alkylethers of vinyl alcohols; styrene and ring substituted styrene derivatives; vinyl monomers; and any combinations thereof.

9. The macroporous electro-responsive cryogel of claim 7, wherein the charged monomers are acrylic acid, the uncharged monomers are acrylamide, and the cross-linker monomers are N,N'-methylenebis-acrylamide or polyethyleneglycol di(meth)acrylate.

10. The macroporous electro-responsive cryogel of claim 7, wherein the uncharged monomers are about 0.5% to about 5% by weight, volume or mol of the aqueous solution.

11. The macroporous electro-responsive cryogel of claim 7, wherein the ratio of charged monomers to uncharged monomers is from about 5:0.5 to about 1:1 by weight, volume or mol.

12. The macroporous electro-responsive cryogel of claim 1, wherein the aqueous solvent is selected from the group consisting of water and mixtures of water and water-miscible organic solvents.

13. The macroporous electro-responsive cryogel of claim 1, wherein the cryogel further comprises a compound selected from the group consisting of a small organic molecule; a small inorganic molecule; a saccharine; an oligosaccharide; a polysaccharide; a biological macromolecule; a nucleic acid; a nucleic acid analog and derivative; an extract made from biological materials; an animal tissue; a naturally occurring or synthetic composition; and any combinations thereof.

14. The macroporous electro-responsive cryogel of claim 13, wherein the compound is a therapeutic agent, a biological cell, or a detectable molecule.

15. The macroporous electro-responsive cryogel of claim 1, wherein the polymerization reaction is carried out at a temperature at least 5° C. below the freezing temperature of the aqueous solvent.

16. The macroporous electro-responsive cryogel of claim 1, wherein the cryogel comprises pores having a mean pore diameter in a range of about 0.01 µm to 1000 µm.

17. The macroporous electro-responsive cryogel of claim 1, wherein the cryogel has a porosity of 0.1 to 0.99.

18. A method for preparation of an electro-responsive cryogel of claim 1, the method comprising: polymerizing an aqueous solution of charged monomers and cross-linker monomers under freezing at temperature below the freezing temperature of aqueous solvent.

19. A method for controlling the release of a bioactive agent, the method comprising: (a) providing a macroporous electro-responsive cryogel of claim 1, wherein the cryogel comprises the bioactive agent; and (b) inducing a change in porosity, pore size, pore connectivity, swelling agent concentration, and/or specific volume of the composition via an electrical stimulus to control the release of the bioactive agent.

20. The macroporous electro-responsive cryogel of claim 1, wherein the cryogel is capable of collapsing within tens of seconds in response to the electrical stimulus.

21. The macroporous electro-responsive cryogel of claim 1, wherein the cryogel is capable of collapsing to less than 5% of the original area in response to the electrical stimulus.

22. The macroporous electro-responsive cryogel of claim 1, wherein the cryogel is capable of collapsing reversibly in response to the electrical stimulus.

23. The macroporous electro-responsive cryogel of claim 13, wherein the cryogel is capable of delivering the compound in a triggered and stimulus-proportioned manner.

24. The macroporous electro-responsive cryogel of claim 11, wherein the ratio of charged monomers to uncharged monomers is from about 8:4 to about 1:1 by weight, volume or mol.

25. The macroporous electro-responsive cryogel of claim 13, wherein the compound is a therapeutic agent.

\* \* \* \* \*